(12) United States Patent
Pinnavaia et al.

(10) Patent No.: US 6,391,278 B1
(45) Date of Patent: *May 21, 2002

(54) CATALYTIC APPLICATIONS OF MESOPOROUS METALLOSILICATE MOLECULAR SIEVES AND METHODS FOR THEIR PREPARATION

(75) Inventors: Thomas J. Pinnavaia; Peter T. Tanev; Wenzhong Zhang; Jialiang Wang, all of East Lansing; Malama Chibwe, Lansing, all of MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/246,739

(22) Filed: Feb. 8, 1999

Related U.S. Application Data

(63) Continuation of application No. 08/797,718, filed on Feb. 11, 1997, now Pat. No. 6,193,143, and a continuation of application No. 08/527,504, filed on Sep. 13, 1995, now Pat. No. 5,672,556, which is a division of application No. 08/409,173, filed on Mar. 23, 1995, now Pat. No. 5,712,402, which is a continuation-in-part of application No. 08/355,979, filed on Dec. 14, 1994, now Pat. No. 5,840,264, which is a continuation-in-part of application No. 08/293,806, filed on Aug. 22, 1994, now abandoned.

(51) Int. Cl.$^7$ .............................................. C01B 33/44
(52) U.S. Cl. ................... 423/718; 423/326; 423/328.2; 423/329.1; 423/705
(58) Field of Search ........................... 502/63, 64, 232, 502/240; 423/326, 328.2, 329.1, 705, 718

(56) References Cited

U.S. PATENT DOCUMENTS

| | | | |
|---|---|---|---|
| 4,410,501 A | | 10/1983 | Taramasso et al. |
| 4,480,135 A | | 10/1984 | Esposito et al. |
| 5,098,684 A | | 3/1992 | Kresge et al. |
| 5,102,643 A | | 4/1992 | Kresge et al. |
| 5,143,879 A | | 9/1992 | Whitehurst |
| 5,156,829 A | * | 10/1992 | McCullen et al. .......... 423/718 |
| 5,250,282 A | * | 10/1993 | Kresge et al. .............. 423/705 |
| 5,840,264 A | * | 11/1998 | Pinnovaia et al. .......... 423/277 |
| 6,193,943 B1 | * | 2/2001 | Pinnavaia et al. ....... 423/329.1 |

FOREIGN PATENT DOCUMENTS

| | | |
|---|---|---|
| EP | 100119 | 2/1984 |
| GB | 2116974 | 10/1983 |
| SU | 1747434 | 7/1992 |

OTHER PUBLICATIONS

Beck et al., Chem. Mater., 6, 1816–1821 (1994).

Horvath and Kawazoe, J. of Chem. Eng. of Japan 470–475 (1983).

Sheldon, R. T. in New Developments in Selective Oxidation, Eds. Centi G. and Trifiro F. Elsevier Sci. Publ. B. V., Amsterdam pp. 1–29 (1990).

Nishinaga, A., et al., Chem. Lett. 4, 817–820 (1994).

Mari, et al., Chemom. Intell. Lab. Syst. 22(2) 257–263 (1994).

Chibwe, et al., J. Chem. Soc., Chem. Commun. 3, 278–280 (1993).

Breck, D. W., Zeolite Molecular Sieves: Structure, Chemistry and Use; Wiley and Sons; London (1974).

Meier, et al., Atlas of Zeolite Structure Types, Butterworth, London (1992).

Gies, et al., Zeolites, vol. 12, 42–49 (1992).

Davis, et al., J. Phys. Chem. 98, 4647–4653 (1994).

Jacobs, P. A., et al., Nature, 345, 240–242 (1990).

Tuel, et al., Appl. Catal., A: 118 (2) 173–186 (1994).

Reddy, et al., J. Catal., 130, 440–446 (1991).

Corma, et al., J. Chem. Soc. Chem. Commun., 589–590 (1992).

Davis, et al., J. Chem. Soc. Chem. Commun. 745–747 (1992).

Anderson, et al., Nature, 367, 347–351 (1994).

Reddy, et al., Catal. Lett. 28, 263–267 (1994).

Rao et al., J. Catal. 141(2) 604–611 (1993).

(List continued on next page.)

Primary Examiner—Stuart L. Hendrickson
(74) Attorney, Agent, or Firm—Ian C. Mcleod

(57) ABSTRACT

A neutral templating route to mesoporous molecular sieves based on H-bonding and self-assembly between neutral primary amine or diamine surfactants (S°) and neutral inorganic precursors (I°) has been used to prepare hexagonal and lamellar mesoporous silicas with site isolated transition metal centers. This templating approach allows for the preparation of hexagonal or hexagonal-like mesoporous oxidation catalysts with large framework wall thickness of at least about 17 Å, small elementary particle size ($\leq 400$ Å), and unique combinations of framework-confined mesopores and textural mesopores while at the same time providing for facile recovery of the neutral template by simple solvent extraction. The templating of neutral metallosilicate precursors (I°) with neutral diamine surfactants (S°—S°) affords thermally stable pillared lamellar metallosilicates exhibiting complementary framework-confined microporosity and textural mesoporosity while at the same time also providing for template recovery by solvent extraction. In addition, a hexagonal transition metal-substituted catalysts, analogous to MCM-41, have been prepared using the mediated $S^+X^-I^+$ templating pathway (Pathway 3) and mild reaction conditions.

18 Claims, 8 Drawing Sheets

OTHER PUBLICATIONS

Beck, et al., J. Am. Chem. Soc., vol. 114, 10834–10843 (1992).

Inagaki et al., J. Chem. Soc. Chem. Commun., vol. 8, 680–682 (1993).

Stucky et al., (Nature, vol. 368, 317–321 (1994).

Corma et al, J. Chem. Soc. Chem. Commun. 147–148 (1994).

Pinnavaia et al., Nature, vol. 368, 321–323 (1994).

Coustel et al., J. Chem. Soc., Chem. Commun., 967–968 (1994).

Chavin, et al., J. Catal., vol. 111, 94–105 (1988).

Sing et al., Pure Appl. Chem. vol. 57, 603–619 (1985).

Perspectives in Molecular Sieve Science, Eds. Flank, W. H. and White T. E. Jr., ACS Symposium series No. 368, W. D. C. p. 247:524:544 (1988).

Gunnawardance et al., Zeolites, vol. 8, 127–131 (1988).

Davis et al., XIII North American Meeting of the Catalysis Soc., Book of Abstracts, p.D14 (1993).

Sing et al., J. Chem. Soc., Chem. Commun., 1257–1258 (1993).

Cartlidge et al., Zeolities, vol. 9, 346–349 (1989).

Thangaraj et al., Zeolites, vol. 9, 943–950 (1992).

\* cited by examiner

| hkl | d(A) |
|-----|------|
| 100 | 32.6 |
| 110 | 19.2 |
| 200 | 16.7 |
| 210 | 12.5 |

Ti-MCM-41
$S^+X^-I^+$

CATALYTIC APPLICATIONS OF MESOPOROUS METALLOSILICATE MOLECULAR SIEVES AND METHODS FOR THEIR PREPARATION

CROSS-REFERENCE TO RELATED APPLICATIONS

This application is a continuation of application Ser. No. 08/797,718 filed on Feb. 11, 1997, now U.S. Pat. No. 6,493,143, which is a division of Ser. No. 08/409,173, filed Feb. 23, 1995, now U.S. Pat. No. 5,712,402, which is a CIP of Ser. No. 08/355,979, filed Dec. 14, 1994, now U.S. Pat. No. 5,840,264, which is a CIP of Ser. No. 08/293,806 filed Aug. 22, 1994 and Ser. No. 08/527,504, filed Sep. 13, 1995, now U.S. Pat. No. 5,672,556 now abandoned.

U.S. GOVERNMENT RIGHTS

The invention described in this application was sponsored by the National Science Foundation Contract CHE-9224102. The U.S. Government has certain rights to this invention.

BACKGROUND OF THE INVENTION (1) Field of the Invention

This invention relates to the synthesis of novel metal-substituted mesoporous molecular sieves and to their use as a catalysts for peroxide hydroxylation of benzene and oxidation of large substituted aromatics. Specifically the mesoporous molecular sieve catalysts of the present invention are prepared by a neutral S° I° self-assembly method comprising steps of hydrogen H-bonding between neutral amine (S°) or diamine (S°—S°) template and neutral inorganic oxide precursors (I°), followed by hydrolysis and crosslinking under mild reaction conditions. The new templating approach ensures the preparation of hexagonal or hexagonal-like oxidation catalysts exhibiting large framework wall thickness of at least about 17 Å, small elementary particle size ($\leq 400$ Å), and unique combinations of framework-confined uniform mesopores and textural mesopores. In addition, the invention provides for the synthesis of thermally stable pillared lamellar metallosilicates by neutral templating method involving neutral metallosilicate precursors (I°) and neutral diamine surfactants (S°—S°). The invention also provides for efficient recovery and recycling of the neutral template by simple solvent extraction methods. This invention also demonstrates the preparation of transition metal-substituted hexagonal MCM-41 silica using mediated S$^+$X$^-$I$^+$ templating route and mild reaction conditions.

The invention also relates to a catalytic application of these mesoporous metallosilicates for peroxide oxidation of substituted aromatics with kinetic diameters that are too large (larger than 6 Å) to access the pore structure of the conventional microporous transition metal-substituted silicates such as titano- and vanadosilicalites.

(2) Description of Related Art

One of the most important methods for converting hydrocarbons to useful industrial chemicals, intermediates and pharmaceuticals is catalytic oxidation. Currently, stoichiometric oxidations with inorganic oxidants, such as permanganate and dichromate, are carried out on a large scale in the manufacture of fine chemicals. However, these oxidation routes generate large amounts of waste inorganic salts (pollutants) that are extremely difficult to dispose of and economically impractical to recycle. In addition, these classical oxidation processes exhibit low selectivity and thus involve as an indispensable part of the synthesis a costly separation of the side products. Therefore, there is a growing demand for developing cleaner, catalytic and much more selective alternatives to existing oxidation processes. For example, the classical multistep process of production of hydroquinone from benzene involves the following steps: (i) preparation of aniline from benzene by nitration and reduction in order to generate a functional group that can be easily oxidized; (ii) oxidation with stoichiometric amounts of $MnO_2$ (iii) reduction with Fe/HCl (Sheldon R. T. in *New Developments in Selective Oxidation,* Eds. Centi G. and Trifiro F., Elsevier Sci. Publ. B. V., Amsterdam, (1990) pp. 1–29). The amount of generated waste is huge—about 10 kg of inorganic salts ($MnSO_4$, $FeCl_2$, $Na_2SO_4$, NaCl) per kg of hydroquinone product.

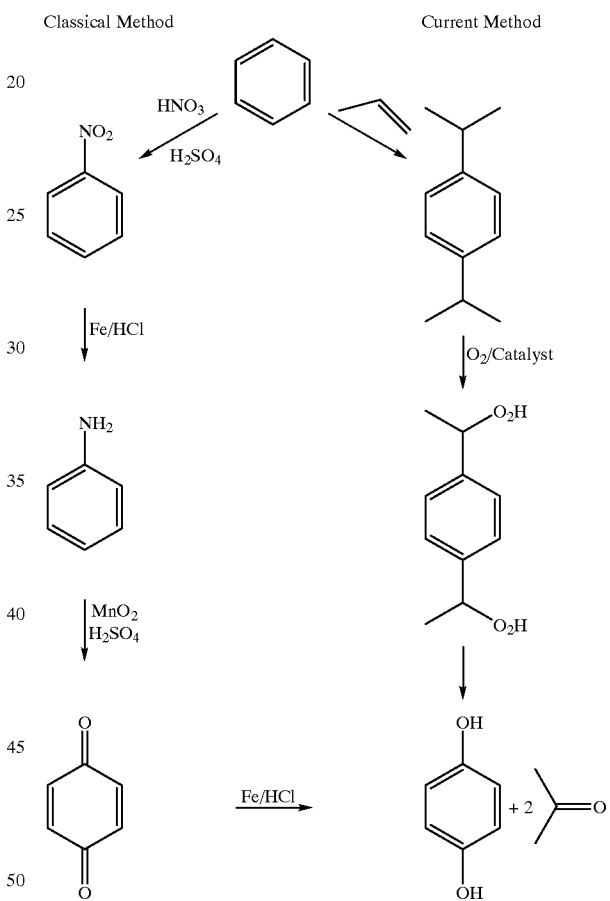

The current catalytic process on the other hand, uses three steps with the initial step being benzene alkylation to 1,4-diisopropylbenzene followed by catalytic oxidation and acid catalyzed rearrangement of the bis-hydroperoxide. It is estimated that the latter process produces about 10% of inorganic salts formed by the classical process (i. e.>1 kg inorganic salts per kg hydroquinone). It is clear that the classical multistep process leads to huge production of waste by-products. On the other hand the existing catalytic process still generates some waste and organic by-products as a result of oxidatively eliminating the isopropyl groups from the 1,4-diisopropylbenzene. In summary, the disadvantages of the classical method are that it generates large amount of pollutants, the oxidant is difficult if not impossible to recover and the selectivity is very low. On the other hand the disadvantages of the existing catalytic process are that it involves multistep transformations, still generates significant amount of pollutants and difficult to separate by-products. Therefore, a one or two step selective catalytic oxidation process to hydroquinone is highly desirable. Such a catalytic process has been recently disclosed (U.S. Pat. No. 4,410,501) and industrially implemented in Italy by Enichem. The high selectivity toward hydroquinone was achieved by performing a liquid phase peroxide oxidation of phenol in the micropores (approximately 6 Å in size) of the titanium substituted molecular sieve-silicalite (denoted TS-1). Another important advantage of this heterogeneous catalytic system is that the catalyst is stable and can be recovered and recycled.

However, the catalytic oxidation of a much larger organic entities such as 2,6-di-tert-butylphenol (with kinetic diameter of approximately 10 Å) is currently performed only by a homogeneous catalytic routes employing different organometallic complex catalysts such as: Co(disalicylidenepropylenetriamine) disclosed by Nishinaga, A. et al. *Chem. Lett.* 4, 817–820 (1994); binuclear Cu(II).mu.-hydroxo complexes with nitrogen chelating ligands (Mari et al. *Chemom. Intell. Lab. Syst.* 22(2) 257–263 (1994)); a phase-transfer catalysts such as 18-crown-6, 18-dibenzocrown-6, triethylbenzylammonium chloride (U.S. Pat. No. 1747434) and metalloporphyrins or intercalated metalloporphyrins such as Cobalt(II) phthalocyanine-tetrasulfonate intercalated into a $Mg_5Al_{2.5}$-layered double hydroxide (LDH)-Chibwe et al., *J. Chem. Soc., Chem. Commun.* 3, 278–280 (1993). However, the use of homogeneous catalysts has the following major disadvantages: (i) these catalysts are usually very expensive, highly toxic and difficult to separate and to recover from the reaction product and (ii) the catalytic oxidation of the 2,6- di-tert-butylphenol over these metal complexes proceeds primarily to the 3,3', 5,5'-tetra(tert-butyl)-4,4'-diphenoquinone dimer rather to the more desirable 2,6-di-tert-butylbenzoquinone monomer, i.e. the selectivity to the corresponding monomer is very low. One way to solve the separation problem, as taught by Chibwe et al., ibid, is to encapsulate these metal complex catalysts in inorganic matrix (such as LDH) and to be able to recover and recycle the catalyst. However, the large scale industrial application of the above processes and the use of expensive and toxic catalysts is still little justified due to the low selectivity toward mono-benzoquinone and separation problems. A very promising way to improve the selectivity toward monomeric benzoquinone would be to limit the size of the active complex, i.e. the size of the reaction product, by performing the oxidation of the large aromatic substrate into the uniform mesopores of a transition metal-substituted porous molecular sieve material.

Porous materials created by nature or by synthetic design have found great utility in all aspects of human activity. The pore structure of the solids is usually formed in the stages of crystallization or subsequent treatment. Depending on their predominant pore size, the solid materials are classified as: (i) microporous, having pore sizes <20 Å; (ii) macroporous, with pore sizes exceeding 500 Å; and (iii) mesoporous, with intermediate pore sizes between 20 and 500 Å. The use of macroporous solids as adsorbents and catalysts is relatively limited due to their low surface area and large non-uniform pores. Microporous and mesoporous solids, however, are widely used in adsorption, separation technology and catalysis. Owing to the need for higher accessible surface area and pore volume for efficient chemical processes, there is a growing demand for new highly stable mesoporous materials. Porous materials can be structurally amorphous, paracrystalline, or crystalline. Amorphous materials, such as silica gel or alumina gel, do not possess long range order, whereas paracrystalline solids, such as γ- or $Al_2O_3$ are quasiordered as evidenced by the broad peaks on their X-ray diffraction patterns. Both classes of materials exhibit a broad distribution of pores predominantly in the mesoporous range. This wide pore size distribution limits the shape selectivity and the effectiveness of the adsorbents, ion-exchanges and catalysts prepared from amorphous and paracrystalline solids.

The only class of porous materials possessing rigorously uniform pore sizes is that of zeolites and related molecular sieves. Zeolites are microporous highly crystalline aluminosilicates. Their lattice is composed by $TO_4$ tetrahedra (T=Al and Si) linked by sharing the apical oxygen atoms. Their pore network, which is confined by the spatially oriented $TO_4$ tetrahedra, consists of cavities and connecting windows of uniform size (Breck D. W., *Zeolite Molecular Sieves: Structure, Chemistry and Use;* Wiley and Sons; London, 1974). Because of their aluminosilicate composition and ability to discriminate small molecules, zeolites are considered as a subclass of molecular sieves. Molecular sieves are crystalline nonaluminosilicate framework materials in which Si and/or Al tetrahedral atoms of a zeolite lattice are substituted by other T atoms such as B, Ga, Ge, Ti, V, Fe, or P.

Zeolite frameworks are usually negatively charged due to the replacement of $Si^{4+}$ by $Al^{3+}$. In natural zeolites this charge is compensated by alkali or alkali earth cations such as $Na^{30}$, $K^{30}$ or $Ca^2$. In synthetic zeolites the charge can also be balanced by ammonium cations or protons. Synthetic zeolites and molecular sieves are prepared usually under hydrothermal conditions from alumosilicate or phosphate gels. Their crystallization, according to the hereafter discussed prior art, is accomplished through prolonged reaction in an autoclave for 1–50 days and, often times, in the presence of structure directing agents (templates). The proper selection of template is of extreme importance for the preparation of a particular framework and pore network. A large variety of organic molecules or assemblies of organic molecules with one or more functional groups are known in the prior art to give more than 85 different molecular sieve framework structures. (Meier et al., *Atlas of Zeolite Structure Types,* Butterworth, London, 1992). An excellent up to date review of the use of various organic templates and their corresponding structures, as well as the mechanism of structure directing is given for example in Gies et al., *Zeolites,* vol. 12, 42–49 (1992). Due to their uniform pore size, unique crystalline framework structure and ability for isomorphous substitution synthetic zeolites and molecular sieves are extremely suitable for a number of adsorption, separation and catalytic processes involving organic molecules. Recently, it has been discovered that synthetic zeolites and molecular sieves can be functionalized by partially substituting the framework T-atoms with such metal atoms capable of performing different chemical (mostly catalytic) tasks. As a result a large variety of highly selective catalysts have been reported during the last decade. In the spectrum of molecular sieve catalyst a special place is occupied by the metal-substituted, high silica molecular sieves (Si/Al ratio>5). Such molecular sieves are highly hydrophobic and therefore exhibit high affinity toward organic molecules. Among these important materials the microporous Ti-substituted high silica molecular sieve, silicalite-1 (denoted TS-1), with MFI structure and pore size of ≈6 Å is quickly emerging as a valuable industrial catalyst due to its ability to oxidize organic molecules at mild reaction conditions.

The hydrothermal synthesis of a TS-1 was first disclosed by Taramasso et al in U.S. Pat. No. 4,410,501. According to this prior art TS-1 was prepared by prolonged hydrothermal treatment (175° C. for two to 10 days) of a reaction mixture consisting of a tetraethylorthosilicate (TEOS) as a source of silica, tetraethylorthotitanate (TEOT) as a source of Ti and tetrapropylammonium hydroxide (TPAOH) as a template or structure directing agent. However, a positively charged quaternary ammonium ion template ($S^+$) was used in order to assemble the Ti-silicalite framework by base catalyzed hydrolysis of the inorganic alkoxides. The base catalyzed hydrolysis of the inorganic alkoxide affords a pentacoordinated transition state (via a nucleophilic attack on the T atom by $OH^-$), giving $[T(alkoxy)_4OH]^-$, and finally reactive intermediate of the type $T(alkoxy)_{4-x}(OH)_x$. Thus, the silicalite framework is most likely formed by condensation of $I^-$species of the type $[TO_x(OR)_{4-x}]^-$ (where R is alkyl or hydrogen) around single quaternary ammonium cations ($S^+$). The charge balance in the final templated product is achieved by coupling of the $S^+$ and $OH^-$ ion pairs in the cavity of silicalite framework with only van der Waals interactions existing between the neutral silicate framework and the occluded template. The preparation of TS-1, as described in Example 2 of this prior art, clearly involves $S^+I^-$ electrostatic templating forces between the cationic quaternary ammonium template ($S^+$) and the negatively charged silica precursor ($I^-$), such as ammonium stabilized LUDOX TM-AS-40 from DuPont Inc. Example 8 represents yet another illustration of the $S^+ I^-$TS-1 preparation with the negative charge on the inorganic oxide precursor coming from the partial substitution of $Si^{4-}$ for $Al^{3+}$. Numerous reports in the recent literature (see for example Davis et al, *J. Phys. Chem.* 98, 4647–4653 (1994)) point out that the charged $TPA^+$ template species are strongly geometrically (and electrostaticly in the case of Al-substituted TS-1) confined to the cavities of the silicalite framework and that the only way to remove the template is to destroy it by calcination of the crystalline material in air at 550° C. The 96 tetrahedra per unit cell of silicalite propagate in 3 dimensions to reveal a system of intersecting framework-confined micropores composed of 10-membered parallel elliptical (5.1×5.7Å) channels along [100] and zig-zag nearly circular (5.4±0.2 Å) channels along [010]. The specific surface area and total pore volume of TS-1 are usually in the range of 328 to 485 m²/g and 0.096 to 0.136 g/g (n-hexane), respectively. The full $N_2$ adsorption-desorption isotherms of TS-1 exhibits typical Langmuir character. Occasionally, depending on the preparation conditions, a poorly developed hysteresis loop in the Pi/Po>0.4 region is observed. This hysteresis loop most likely corresponds to capillary condensation in nonuniform textural mesopores. However, the presence of textural mesopores would not significantly influence the catalytic oxidation properties of TS-1 toward large substituted aromatics (with kinetic diameters>6 Å) since they can not penetrate into the framework-confined micropores and undergo catalytic transformation. The size of the framework-confined micropores of TS-1 is equal to the size of the parallel elliptic and intersecting zig-zag channels (~6 Å).

TS-1 was found to be an effective oxidation catalyst for a variety of organic compounds using aqueous hydrogen peroxide as oxidant. Prior art examples include oxidation of alkanes (P. A. Jacobs et al, *Nature*, 345, 240–242 (1990)), oxidation of primary alcohols to aldehydes and secondary alcohols to ketones (U.S. Pat. No. 4,480,135), epoxidation of olefins (Eur. Pat. No. 100,119), hydroxylation of aromatic compounds (G.B.R. Pat. No. 2,116,974 and Tangaraj et al, *Appl. Catal.* 57 (1990) L1) and oxidation of aniline (Tuel et al., *Appl. Catal.*, A: 118(2) 173–186 (1994)). It is speculated that the catalytic activity of the TS-1 is related directly to the presence of site isolated titanium in the silicate framework. However, because of the small pore size the number of the organic compounds that can be oxidized by TS-1 is strongly limited to molecules having kinetic diameters equal to or less than about 6 Å. Another titanium silicalite, TS-2, with MEL structure was recently reported to exhibit similar oxidation properties (Reddy et al, *J. Catal.*, 130, 440–446 (1991)). The preparation of this molecular sieve again involved the use of charged ($S^+$) quaternary ammonium template ($TBA^+$) and prolonged hydrothermal conditions. The similar catalytic behavior of TS-2 is not surprising in view of the nearly identical size of the silicalite-2 framework-confined micropore channels (~5.3 Å). Very recently, a Ti-substituted analog of yet another zeolite (zeolite β) with slightly larger micropore size has been disclosed by Corma et al., *J. Chem. Soc. Chem. Commun.*, 589–590 (1992). The synthesis of this $Al^{3+}$ containing zeolite was accomplished by hydrothermal treatment of a reaction mixture containing again an ionic reactants such as $Al(NO_3)_3$, amorphous silica (which at the alkaline pH of the synthesis will slowly dissolve giving most likely a negatively charged ($I^-$) silica species) and a cationic template (TEAOH). Therefore, this oxidation catalyst can also be classified as prepared by the $S^{30}I^-$ electrostatic templating approach. The main incentive for preparing Ti-substituted analog of zeolite b was to be able to take advantage of its slightly larger micropore size pore network composed by intersecting 12-membered ring (7.6×6.4 Å) channels along [001] and 12-membered channels (5.5 Å) along [100]. However, the catalytic oxidation chemistry of Ti-substituted zeolite β, with the exeption of the slightly higher conversion toward cyclododecane than TS-1, was again confined to the well known small substrates subjectable to catalytic oxidation over TS-1 and TS-2 molecular sieves. In addition, the presence of $Al^{3+}$ in the zeolite β affords a hydrophilic framework exhibiting much higher acidity than TS-1 and TS-2. This precludes the possibility for catalytic oxidations of bulky alkyl substituted aromatics or phenols without dealkylation of the alkyl groups. The small micropore size of two recently discovered Ti-substituted molecular sieves, both prepared by electrostatic templating, namely ETS-10 (Anderson et al., *Nature*, 367, 347–351 (1994)) and Ti-ZSM-48 (Davis et al., *J. Chem. Soc. Chem. Commun.* 745–747 (1992)), would most likely confine their catalytic oxidation chemistry again to substrates with kinetic diameters smaller than 6 Å.

Finally, V-substituted silicalite-1 and 2 (denoted VS-1 and VS-2) oxidation catalysts were also reported very recently (see for example Reddy et al., *Catal. Lett.* 28, 263–267 (1994) and Rao et al, *J. Catal.* 141(2) 604–611 (1993)). However, due to the embedding of V in the same silicalite microporous framework the catalytic oxidation activity of these molecular sieves was again limited to small organic substrates with kinetic diameters of less than 6 Å.

In summary, all prior art microporous molecular sieve peroxide oxidation catalysts are prepared by $S^+I^-$ templating route involving electrostatic interactions between positively charged templates ($S^+$) and negatively charged inorganic oxide precursors ($I^-$). The condensation of the microporous framework was accomplished by a prolonged hydrothermal treatment around a single charged surfactant species ($S^+$). Due to the strong electrostatic interactions (for $Al^{3+}$ substituted materials) or geometric confinement (for pure Si materials) the charged template is strongly bonded or occluded into the microporous framework and impossible to recover. Finally, due to the small framework micropore size of the prior art molecular sieves the site isolated transition metal centers (such as Ti or V) were accessible by and active only for peroxide oxidations of small organic molecules (such as alkanes, cycloalkanes, alcohols, olefins, benzene, phenol or aniline with kinetic diameters less that about 6 Å).

Therefore, there is a need for a new transition metal-substituted mesoporous molecular sieves capable of catalyzing the oxidation of organic species with kinetic diameters>6 Å, especially substituted aromatics. Such transition metal-substituted mesoporous molecular sieves would greatly complement and extend the catalytic chemistry of prior art titanium and vanadium silicalites toward much larger aromatic compounds.

A breakthrough toward the preparation of mesoporous molecular sieves have been disclosed recently in U. S. Pat. Nos. 5,098,684; 5,102,643. The claimed class of mesoporous materials (denoted as M41S) was found to possess uniform and adjustable pore size in the range of 13–100 Å. In addition, these materials exhibited a small framework wall thickness of from 8 to 12 Å and elementary particle size of usually much larger than 500 Å. Depending on preparation conditions M41S materials with hexagonal (MCM-41), cubic (MCM-48) or layered crystallographic structure have been disclosed (Beck et al., *J. Am. Chem. Soc.,* vol. 114, 10834–10843 (1992). The most regular preparations of this prior art give an X-ray diffraction pattern with a few maxima in the extreme low angle region. The positions of these maxima in the case of MCM-41 fit the positions of the hk0 reflections of the hexagonal lattice (namely 100, 110, 200 and 210). In addition to that these materials show very characteristic electron diffraction pattern with approximately hexagonal arrangement of diffraction maxima. The postulated mechanism of formation of these molecular sieves involves strong electrostatic interactions and ion pairing between quaternary ammonium liquid crystal cations, as structure directing agents, and anionic silicate oligomer species (U.S. Pat. No. 5,098,684). Related mesoporous structures also have been prepared by rearrangement of a layered silicate (kanemite) (Inagaki et al., *J. Chem. Soc. Chem. Commun.,* vol. 8, 680–682 (1993)) in the presence of quaternary ammonium cations. Recently, Stucky et al. (*Nature,* vol. 368, 317–321 (1994)) extended the electrostatic assembly approach by proposing four complementary synthesis pathways. Pathway 1 involved the direct co-condensation of anionic inorganic species ($I^-$) with a cationic surfactant ($S^+$) to give assembled ion pairs ($S^+I^-$), the original synthesis of MCM-41 being the prime example (U.S. Pat. No. 5,098,684). In the charge reversed situation (Pathway 2) an anionic template ($S^-$) was used to direct the self-assembly of cationic inorganic species ($I^+$) via $S^{31}I^+$ ion pairs. The pathway 2 has been found to give a hexagonal iron and lead oxide and different lamellar lead and aluminum oxide phases (Stucky et al., ibid). Pathways 3 and 4 involved counterion ($X^{31} M^+$) mediated assemblies of surfactants and inorganic species of similar charge. These counterion—mediated pathways afforded assembled solution species of type $S^+X^-I^+$ (e.g., $X^-=Cl^-$, $Br^-$) or, $S^-M^+I^-$ (e.g., $M^+=Na^+$, $K^+$), respectively. The viability of Pathway 3 was demonstrated by the synthesis of a hexagonal MCM-41 using a quaternary ammonium cation template and strongly acidic conditions (5–10 M HCl or HBr) in order to generate and assemble positively-charged framework precursors (Stucky et al., ibid). In another example, a condensation of anionic aluminate species was accomplished by alkali cation mediated ($Na^+$, $K^+$) ion pairing with an anionic template ($C_{12}H_{25}OPO_3^-$). The preparation of the corresponding lamellar Al(OH)$_3$ phase in this case has been attributed to the fourth pathway ($S^-M^+I^-$). The preparation of Ti-substituted analog of MCM-41 was first demonstrated by Corma et al., *J. Chem. Soc. Chem Commun.* 147–148 (1994). However, this prior art applies the $S^+I^-$ (Pathway 1) templating route and prolonged hydrothermal synthesis conditions in order to prepare the Ti-MCM-41 analog. In addition, the catalytic activity of this particular material was illustrated by the epoxidation of rather small organic molecules such as hex-1-ene (in the presence of $H_2O_2$) and the tertbutyl peroxide oxidation of norbornene. Simultaneously, we have reported (Pinnavaia et al., *Nature,* vol. 368, 321–323 (1994)) the preparation of a hexagonal or hexagonal-like mesoporous silica molecular sieve and a Ti-substituted analog (Ti-HMS) by acid catalyzed hydrolysis of inorganic alkoxide precursors in the presence of a partially protonated primary amine surfactants ($S^°/S^+$). In the same work we have also demonstrated the first ambient temperature preparation of Ti-MCM-41 molecular sieve using different $S^+X^-I^+$ (Pathway 3) templating route. We also reported that both Ti-HMS and Ti-MCM-41 exhibit remarkable catalytic activity toward peroxide oxidation of very large aromatic substrates such as 2,6-DTBP. Here the term "hexagonal" was selected to describe the materials that exhibit in addition to the first $d_{100}$ reflection at least some of the remaining reflections of the hexagonal phase or a diffuse scattering centered where these reflections (namely 110, 200, 210, etc.) are expected. In this materials the rod-like uniform channels are assembled in such a fashion that each channel in most cases is surrounded by six neighboring channels.

The term "hexagonal-like" was chosen to describe materials that exhibit single $d_{100}$ reflections and no additional reflections or diffuse scattering on their diffraction patterns where the remaining 110, 210 and 200 reflections of the hexagonal phase are expected. This term was also selected to describe materials with deviations from the perfect hexagonal symmetry due to very small scattering domain sizes ($\leq 400$ Å) or due to crystallographic defects or combinations thereof. In this materials the rod-like uniform channels are assembled in such a fashion that each channel is usually surrounded by less than six neighbors due to lattice defects or to small particle size or combination thereof.

Very recently we also have demonstrated (Tanev and Pinnavaia, Science, 267:865–867 (1995)) a new templating route to mesoporous molecular sieves based on H-bonding and self-assembly between neutral primary amine or diamine surfactants ($S^°$) and neutral inorganic precursors ($I^°$) at ambient temperature. Our new $S^°I^°$ templating approach, which we denoted a Pathway 5, is complementary to the above electrostatic templating pathways. When we applied the $S^°I^°$ pathway to the synthesis of hexagonal or hexagonal-like mesoporous silicates (denoted HMS) using a neutral primary amine as the template and tetraethyl orthosilicate as the inorganic reagent we obtained derivatives with thicker framework walls, smaller X-ray scattering domain size, and substantial textural mesoporosity, relative to MCM-41 analogs prepared by an electrostatic $S^+I^-$ or $S^+X^-I^+$ templating pathway. The thicker pore walls are highly desired as improving the thermal and hydrothermal stability (Coustel et al., *J. Chem. Soc., Chem. Commun.,* 967–968 (1994)) of the mesopore framework. The pore walls of the prior art MCM-41 and our HMS materials, as revealed by X-ray diffraction measurements, do not exhibit any crystallographic order, i.e. behave like "amorphous" phase. One skilled in the art will know that thicker "amorphous" walls can give a rise to microporous cavities capable to accommodate small organic molecules. Also, one skilled in the art will know that this could be very important for instance in oxidation of small organic substrates such as benzene. The small particle size and substantial textural mesoporosity are essential for accessing the framework-confined pores and for improving the performance of the obtained adsorbents and catalysts (Pinnavaia et al., ibid; Chavin et al., *J. Catal.*, vol. 111, 94–105 (1988)). In addition, the S°I° pathway allowed for facile recovery of the template by simple solvent extraction, circumventing the need for cation donors or ion pairs to remove the charged template.

Most prior art templating pathways are based on charge matching between ionic organic directing agents and ionic inorganic reagents. The template is strongly bonded to the charged framework and difficult to recover. In the original Mobil approach (U.S. Pat. No. 5,098,684) the template was not recovered, but simply burned off by calcination at elevated temperatures. Recently, it has been demonstrated that the ionic surfactant in Pathway 1 materials could be removed by ion—exchange with acidic cation donor solution (U.S. Pat. No. 5,143,879). Also, the template—halide ion pairs in the framework of acidic Pathway 3 materials were displaced by ethanol extraction (Stucky et al., ibid). Thus, ionic template recovery is possible, provided that exchange ions or ion pairs are present in the extraction process.

Here we disclose a new templating route to transition metal-substituted mesoporous molecular sieves that is complementary to Pathways 1 to 4. Our approach is based on H-bonding and self-assembly between neutral primary amine micelles (S°) and neutral inorganic precursors (I°). This new S°I° templating route, which we denote Pathway 5, affords mesoporous metallosilicates with larger wall thicknesses, small particle sizes and complementary textural mesoporosities relative to Pathway 1 and 3 materials. Both HMS and MCM-41 silicates offer exciting opportunities for the preparation of large pore analogs of the industrially important TS-1 catalyst. We also disclose the catalytic activity of these Ti-HMS and Ti-MCM-41 (prepared by a S$^+$X$^-$I$^+$ route) derivatives for the selective peroxide oxidation of substrates that are too large to access the micropore framework of conventional TS-1, TS-2, VS-1 or VS-2.

Hereafter, in order to clarify one of the objects of the present invention, we would like to define and differentiate the terms framework-confined uniform porosity and textural porosity. Framework-confined uniform pores are pores formed by nucleation and crystallization of the framework elementary particles. These pores typically are cavities and channels confined by the solid framework. The size of the cavities and channels, i.e. the size of the framework-confined uniform pores, in molecular sieve materials is highly regular and predetermined by the thermodynamically favored assembly routes. The framework-confined pores of freshly crystallized product are usually occupied by the template cations and water molecules. While water molecules are easily removed by heating and evacuation the quaternary ammonium cations, due to their high charge density, are strongly bonded or confined to the pore cavities and channels of the negatively charged framework. The same concepts are expected to apply for the charge reversed situation where an anionic template is confined in the pores of a positively-charged framework. Therefore, a cation or anion donor or ion pairs are necessary in order to remove the charged template from the framework of the prior art molecular sieves.

Textural porosity is the porosity that can be attributed to voids and channels between elementary particles or aggregates of such particles (grains). Each of these elementary particles in the case of molecular sieves is composed of certain number of framework unit cells or framework-confined uniform pores. The textural porosity is usually formed in the stages of crystal growth and segregation or subsequent thermal treatment or by acid leaching. The size of the textural pores is determined by the size, shape and the number of interfacial contacts of these particles or aggregates. Thus, the size of the textural pores is usually at least one or two orders of magnitude larger than that of the framework-confined pores. For example, the smaller the particle size, the larger the number of particle contacts, the smaller the textural pore size and vice versa. One skilled in the art of transmission electron spectroscopy (TEM) could determine the existence of framework-confined micropores from High Resolution TEM (HRTEM) images or that of framework-confined mesopores from TEM images obtained by observing microtomed thin sections of the material as taught in U.S. Pat. No. 5,102,643.

One skilled in the art of adsorption could easily distinguish and evaluate framework-confined uniform micropores by their specific adsorption behavior. Such materials usually give a Langmuir type (Type I) adsorption isotherm without a hysteresis loop (Sing et al., *Pure Appl. Chem.*, vol. 57, 603–619 (1985)). The existence of textural mesoporosity can easily be determined by one skilled in the art of SEM, TEM and adsorption. The particle shape and size can readily be established by SEM and TEM and preliminary information concerning textural porosity can also be derived. The most convenient way to detect and assess textural mesoporosity is to analyze the $N_2$ or Ar adsorption-desorption isotherm of the solid material. Thus, the existence of textural mesoporosity is usually evidenced by the presence of a Type IV adsorption-desorption isotherm exhibiting well defined hysteresis loop in the region of relative pressures Pi/Po>0.4 (Sing et al., ibid). This type of adsorption behavior is quite common for a large variety of paracrystalline materials and pillared layered solids.

The microporous transition metal-substituted zeolites and molecular sieves of the prior art exhibit mainly framework-confined uniform micropores, and little or no textural mesoporosity as evidenced by their Langmuir type adsorption isotherms accompanied with poorly developed hysteresis loops at Pi/Po>0.4. The typical values for their specific surface area are from 300–500 m$^2$/g and for the total pore volume$\leq$0.6 cm$^3$/g (*Perspectives in Molecular Sieve Science*, Eds. Flank, W. H. and White T. E. Jr., ACS symposium series No. 368, Washington D. C., p. 247; 524; 544 (1988)). All known microporous high silica metallosilicates are prepared by prolonged crystallization at hydrothermal conditions, using single quaternary ammonium cations or protonated primary, secondary or tertiary amines (S$^+$) to assemble the anionic inorganic species (I$^-$) into a microporous framework. It should also be noted that the use in the prior art of neutral amines and alcohols as templates (Gunnawardane et al., Zeolites, vol. 8, 127–131 (1988)) has led to the preparation of only microporous highly crystalline (particle size>2 μm) molecular sieves that lack appreciable textural mesoporosity. For the mesoporous molecular sieves of the MCM-41 family the uniform mesopores are also framework-confined. This has been verified by TEM lattice images of MCM-41 shown in U.S. Pat. No. 5,102,643. Therefore, the framework of this class of materials can be viewed as a expanded version of a hexagonal microporous framework. The existence of these framework-confined uniform mesopores was also confirmed by the capillary condensation phenomenon observed in their adsorption isotherms. Typical $N_2$ adsorption-desorption isotherm of MCM-41, prepared by $S^+I^-$ templating method (Pathway 1), (Davis et al., *XIII North American Meeting of the Catalysis Soc., Book of Abstracts*, p. D14 (1993)) is included here for reference (FIG. 1). This adsorption isotherm is essentially the same as that obtained previously by Sing et al., *J. Chem. Soc., Chem. Commun.*, 1257–1258 (1993). The isotherm is characterized by a sharp adsorption uptake followed by a hysteresis loop in the Pi/Po region of 0.3 to 0.4. This hysteresis corresponds to capillary condensation into the framework-confined uniform mesopores. The lack of appreciable hysteresis beyond Pi/Po>0.4 implies the absence of textural mesoporosity. This lack of textural mesoporosity is also supported in some cases by the highly ordered hexagonal prismatic shaped aggregates of size >2 μm (Beck et al., *J. Am. Chem. Soc.*, vol. 114, 10834–10843 (1992). The total pore volume of the material reported by Davis et al. is ≈0.7 cm³/g and that of the framework-confined mesopores, as determined from the upper inflection point of that hysteresis loop, is almost equal to that of the total pore volume. Therefore, the ratio of textural to framework-confined mesoporosity here approaches zero. The size of the framework-confined uniform mesopores is ≈30 Å.

Thus, the metallosilicate molecular sieve materials of the aforementioned prior art typically lack appreciable textural mesoporosity. However, there is increasing number of reports in the literature suggesting that textural mesopores behave as a transport pores to the framework-confined uniform pores and that they greatly improve the access and the performance of adsorbents, ion-exchangers and catalysts. This, for example, is demonstrated by Pinnavaia et al., *Nature*, vol. 368, 321–323 (1994); Chavin et al., *J. Catal.*, vol. 111, 94–105 (1988) and in Cartlidge et al., Zeolites, vol. 9, 346–349 (1989). According to this prior art the transport pores provide more efficient assess to the framework-confined pores of the molecular sieve.

In summary, the prior art transition metal-substituted molecular sieves, as well as their preparation approaches have the following disadvantages:

1. The prior art uses charged surfactant ions ($S^+$ or $S^-$) as templates in order to assemble an inorganic molecular sieve framework from charged inorganic oxide precursors ($I^-$ or $I^+$). These charged templates are usually expensive, strongly bonded or geometrically confined to the charged inorganic oxide framework and difficult to recover. In all the prior art examples the electrostatically bonded templates were removed from the framework by either a burning off process or by an ion-exchange reaction with an ion donor solution. Also, ion pairs were necessary in order to extract the template from the framework of Pathway 3 materials.

2. The use of charged templates and hydrothermal synthesis conditions afford the preparation of microporous and mesoporous molecular sieves with large elementary particle size (usually much above 500 Å) and absence of optional balance of framework-confined and textural porosity. This does not contribute to accessing the framework-confined uniform pores. The lack of textural mesoporosity could lead to serious diffusional limitations in many potential applications. The ratio of textural to the framework-confined porosity of these materials is usually close to zero.

3. Another important disadvantage of the prior art mesoporous molecular sieves is their small framework wall thickness (from 8 to 12 Å). This does not contribute to improving the thermal and hydrothermal stability of these prior art materials.

4. Due to the small pore size of the prior art microporous molecular sieve frameworks (such as metallosilicalites) the site isolated transition metal centers (such as Ti or V) were accessible and active only for peroxide oxidation of small organic molecules (such as alkanes, cycloalkanes, alcohols, olefins, benzene, phenol or aniline) with kinetic diameters of less that about 6 Å.

5. The catalytic oxidation of a large substituted aromatics, such as 2,6-di-tert-butylphenol, (with kinetic diameters of approximately 10 Å) is currently performed by a homogeneous catalytic routes employing different organometallic complex catalysts. However, the use of homogeneous catalysts has the following major disadvantages: (i) these catalysts are usually very expensive, highly toxic and difficult to separate and recycle from the reaction product and (ii) the catalytic oxidation of the 2,6-di-tert-butylphenol over these metal complexes proceeds with low selectivity to the 2,6-di-tert-butylbenzoquinone monomer. Therefore, the large scale industrial application of these expensive and toxic catalysts is little justified.

The aforementioned disadvantages of the prior art severely limit the potential industrial applications of these catalytic materials.

Therefore, there is a need for a new metal-substituted mesoporous molecular sieves capable of selectively catalyzing the oxidation of much larger organic species with kinetic diameters>6 Å, especially substituted aromatics or polyaromatics. Such transition metal-substituted mesoporous molecular sieves would greatly complement and extend the catalytic chemistry of prior art microporous titanium and vanadium silicates toward large aromatic molecules. In addition, there is a need for such mesoporous molecular sieve structures exhibiting high thermal and hydrothermal stability (large framework wall thickness), small particle size and complementary framework-confined and textural mesoporosity. Also there is a need for a new preparation art to these ordered mesostructures which would allow for cost reduction by employing less expensive reagents and mild reaction conditions while at the same time providing for the effective recovery and recyclability of the neutral template.

Objects

An object of the present invention is to provide a new $S°$ $I°$ templating route to the design of crystalline, metal-substituted hexagonal or hexagonal-like mesoporous molecular sieves with high thermal stability (large framework wall thickness), small elementary particle size≦400 Å and balanced uniform framework-confined mesoporosity and textural mesoporosity.

Another object of the present invention is to provide a neutral $S° I°$ templating approach to the direct preparation of stable lamellar pillared metallosilicate molecular sieves exhibiting balanced textural and framework-confined microporosity.

Yet another subject of the present invention is to provide inexpensive preparation methods for these catalytic materials by avoiding the use of charged ionic templates and charged inorganic oxide precursors and high temperature hydrothermal synthesis conditions.

Still another object of this invention is to provide for the facile recovery and recycling of the neutral amine ($S°$) or diamine ($S°$—$S°$) template by new separation art involving simple solvent extraction from the crystalline product.

And yet another important object is to demonstrate the preparation of transition metal-substituted hexagonal MCM-41 silica by a $S^+X^-I^+$ templating method (Pathway 3) under mild reaction conditions (ambient temperature synthesis)

and to demonstrate the first catalytic oxidation application of the materials so prepared for peroxide oxidation of large aromatics (kinetic diameter of approximately 10 Å). This differs from all prior art teachings since all known transition metal-substituted MCM-41 materials were prepared by a hydrothermal treatment using Pathway 1 ($S^+I^-$) templating. This teaching is also quite different from all prior art catalytic applications of transition metal-substituted MCM-41 materials since the molecules subjected to catalytic peroxide oxidation were nonaromatic and smaller that the 2,6-di-tert-butyl phenol substrate oxidized in this invention (see Corma et al. *J. Chem. Soc. Chem. Commun.*, 147–148 (1994)).

A very important object of the present invention is to provide a catalytic application of the transition metal-substituted mesoporous molecular sieves of this invention, for peroxide oxidation of substituted aromatics that are too large (with kinetic diameter larger than 6 Å) to access the micropores of the conventional microporous metallosilicates such as TS-1.

Still another objective of the present invention is to provide a catalytically active hetero-atom substituted mesoporous materials for an economically cheaper and viable direct hydroxylation of benzene to phenol than the present multi-step methods.

Applicants know of no prior art teaching the present hexagonal or hexagonal-like metal-substituted mesoporous molecular sieves having large framework wall thickness ($\geq 17$ Å), small particle size ($\leq 400$ Å) and complementary framework-confined uniform mesoporosity and textural mesoporosity. Also, applicants know of no prior art teaching the preparation of these compositions by neutral $S°I°$ templating between nonionic amine template $S°$ and nonionic silicon and metal precursors ($I°$), hydrolysis and crystallization at mild reaction conditions and neutral template recovery and recycling by simple solvent extraction of the templated product.

Also applicants know of no prior art teaching the direct synthesis of stable, pillared lamellar metallosilicate molecular sieves by neutral $S°—S°$ $I°$ templating between nonionic diamine template $S°—S°$ and nonionic mixture of silicon and metal precursors ($I°$), hydrolysis and crystallization at mild reaction conditions and neutral template recovery and recycling by simple solvent extraction of the templated product.

And neither are we aware of mesoporous metallosilicate molecular sieve materials so produced being used for catalytic oxidation of very large organic substrates such as oxidation of 2,6di-t-butyl-phenol to the corresponding quinone.

These and other objects will become increasingly apparent from the following description and the drawings.

SUMMARY OF THE INVENTION

The present invention provides a new class of metal-substituted mesoporous molecular sieve oxidation catalysts. The invention also provides for the preparation of these metal-substituted hexagonal, hexagonal-like or lamellar molecular sieve catalysts by neutral $S°I°$ synthesis route. According to this preparation art the formation of the mesoporous framework is accomplished primarily by H-bonding between neutral silicon and metal precursors ($I°$) and a neutral amine ($S°$) or diamine ($S°—S°$) template, followed by further hydrolysis and crosslinking of $TO_4$ units under mild reaction conditions. This templating approach allows for the preparation of hexagonal or hexagonal-like mesoporous oxidation catalysts with large framework wall thickness of at least about 17 Å, unique combinations of framework-confined and textural mesopores, and small elementary particle size ($\leq 400$ Å), while at the same time providing for facile recovery of the neutral template by simple solvent extraction. The templating of neutral metallosilicate precursors ($I°$) with neutral diamine surfactants ($S°—S°$) affords thermally stable pillared lamellar metallosilicates exhibiting complementary framework-confined microporosity and textural mesoporosity while at the same time also providing for template recovery by solvent extraction. In addition, hexagonal metal-substituted catalysts, analogous to MCM-41, have been prepared using the mediated $S^+X^-I^+$ templating pathway (Pathway 3) and mild reaction conditions.

These new mesoporous metallosilicates, exhibit exceptional catalytic activity for peroxide oxidation of substituted aromatics with kinetic diameters that are too large (larger than 6 Å) to access the pore structure of the conventional microporous transition metal-substituted molecular sieves such as titano- and vanadosilicates.

DESCRIPTION OF PREFERRED EMBODIMENTS

Figure 1:
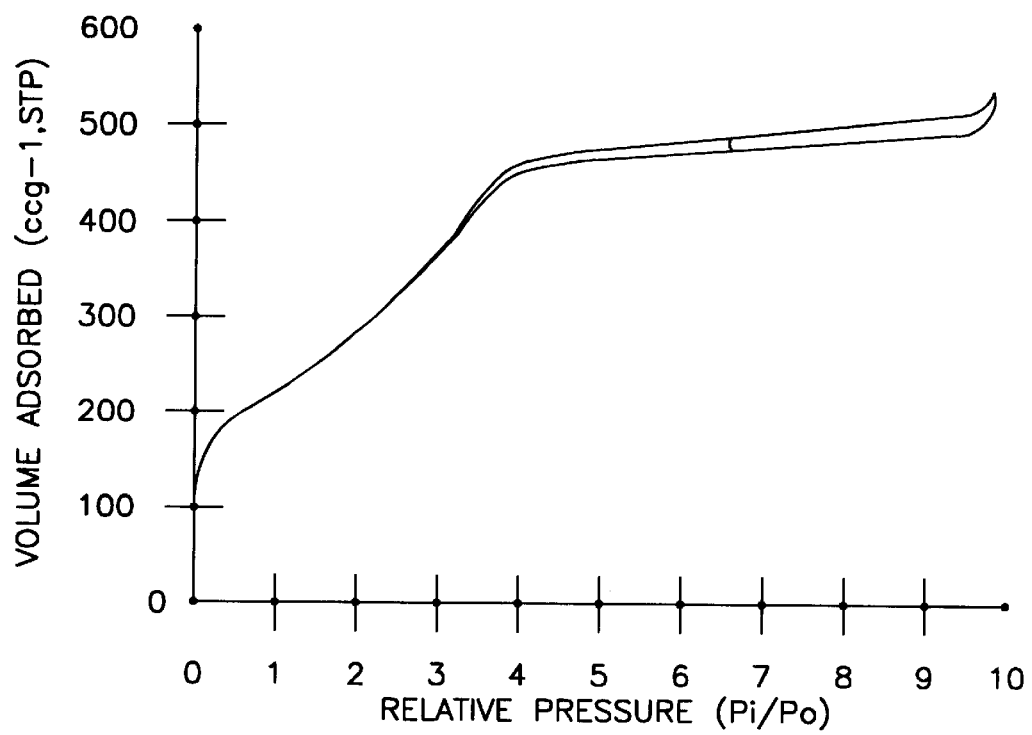
FIG. 1 is a representative $N_2$ adsorption-desorption isotherm for the MCM-41 product from Davis et al., *XIII North American Meeting of the Catalysis Soc., Book of Abstracts*, p. D14 (1993).

The present invention relates primarily to metal-substituted, hexagonal or hexagonal-like mesoporous molecular sieves having large framework wall thickness ($\geq 17$ Å), small elementary particle size ($\leq 400$ Å), a unique combinations of framework-confined mesoporosity and textural mesoporosity, and prepared by a neutral $S°I°$ self-assembly mechanism. This novel templating mechanism comprises reacting a neutral amine template solution ($S°$)

and neutral inorganic oxide precursors solution (I°) to form a reaction product, hydrolysis and aging of the reaction product, and the subsequent removal of the aqueous solution and the template.

Specifically, the present invention relates to a neutral S°I° synthetic route for the preparation of these metal-substituted mesoporous molecular sieves comprising: (a) preparing an aged solution of at least two neutral inorganic oxide precursors (I°) with stirring at a temperature of at least minus 20° C. for at least 5 minutes (aging is optional); (b) preparing a solution of a neutral amine template (S°) with a hydrolyzing agent and co-solvent (optional) with stirring at a temperature between about minus 20° C. and plus 100° C.; mixing of the solutions of steps (a) and (b) at a temperature between about minus 20° C. and plus 100° C. to form a gel which is aged for at least about 30 minutes or longer to form a crystalline product; separating the template and at least some of the hydrolyzing agent from the crystalline product; and optionally calcining the crystalline product at 300 to 1000° C. for at least about 30 minutes.

The present invention provides a new class of hexagonal or hexagonal-like mesoporous metallosilicate molecular sieves with complementary framework-confined uniform and textural mesopores and typically small elementary particle size that can be used as ion-exchangers and catalysts for the catalytic conversion of large organic substrates. This new class of catalytic materials is distinguished from the prior art materials by possessing larger framework wall thickness of $\geq 17$ Å, significant amount of textural mesoporosity, typically very small elementary particle size $\leq 400$ Å and a ratio of textural to framework-confined mesoporosity typically $\geq 0.2$.

In addition, the metal-substituted mesoporous compositions of the present invention are obtained by a new S°I° neutral preparative method. According to the preparation art of this invention the formation of the mesoporous structures is accomplished primarily by H-bonding between a neutral template and a neutral inorganic oxide precursors, followed by further hydrolysis and crosslinking of $T(alkoxy)_{4-x}OH_x$ units, where T represents Si and at least one transition metal, preferably Ti, Cr or V. This H-bonding most likely occurs between any T-OH or T-proton donor compound, and the lone pair of electrons on the central atom of the amine template head group. Specifically, the said method comprises the formation of a reaction system by mixing of a neutral amine (S°) or diamine (S°—S°) template solution with neutral inorganic oxide precursors (I°), preferably inorganic alkoxides or neutral inorganic oxide sols, in the presence of a hydrolyzing agent and a co-solvent (optional), followed by aging and crystallization under stirring at temperature of at least minus 20° C. for at least 0.5 h. Much of the neutral template can be recovered by solvent extraction of the templated product with water or with alcohol, or a mixture thereof, or by vacuum distillation, more preferably by extraction with alcohol. Complete removal of the last traces of template and the further crosslinking of the framework is accomplished by calcination at 300 to 1000° C.

The molar ratio of amine to total inorganic oxide precursors in the initial reaction mixture is between about 0.05 and 3, preferably about 0.25. The mesoporous metallosilicate composition of the present invention preferably has in its as-synthesized and anhydrous state the following formula:

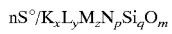

$$nS°/K_xL_yM_zN_pSi_qO_m$$

wherein S° is at least one neutral amine or diamine (S°—S°) such as dodecyl amine or 1,12-diaminododecane; K is optional and is at least one divalent element such as Mg, Zn or Cu; L is optional and is at least one trivalent element such as B, Al, Ga, Cr or Fe; M is optional and is at least one tetravalent element other than silicon such as Ti, V, Sn, Zr or Ge; N is optional and is at least one pentavalent or hexavalent element such as V, W or Mo; O is oxygen and n, x, y, z, p, q and m are the molar parts of S, K, L, M, N, Si and O, respectively. In the solvent extracted and/or calcined composition the molar part of n is preferably 0, x is preferably between 0.001 and 0.2; y is between 0.001 and 0.5; z is between 0.001 and 0.5; p is between 0.001 and 0.5, q is between 0.5 and 1 and m is about 2.

The crystalline mesoporous catalysts of this invention may be characterized as formed by H-bonding between neutral inorganic oxide precursors containing T-OH groups as hydrogen donors and neutral amine templates as hydrogen acceptors, followed by further hydrolysis and crosslinking of $T(alkoxy)_{4-x}OH_x$ units, where T represents Si and at least one transition element such as Ti, V, Cr, W, or Sn, under mild reaction conditions. The t-bonding occurs between any T-OH or generally any T-proton donor group in which the T-inorganic atom is coordinated to "x" groups capable of participating in a H-bonding with the lone pair of electrons on the central atom of the head group of the neutral amine template. Specifically, the method comprises formation of a gel by mixing of a neutral amine template solution with a solution of at least two inorganic oxide alkoxides or inorganic oxide sols or gel precursors in the presence of a hydrolyzing agent and a co-solvent (optional), followed by hydrolysis, aging and crystallization under stirring at temperature of at least minus 20° C. for at least 0.5 h. More particularly, the calcined composition of this invention is characterized by at least one strong X-ray diffraction peak at a d-spacing of at least 15 Å or greater. The said compositions are distinguished in part from prior art MCM-41 materials by a substantially larger framework wall thickness ($\geq 17$ Å) and a much smaller elementary particle size $\leq 400$ Å. More specifically, the mesoporous metallosilicate composition of this invention may be distinguished from those of prior art, including MCM-41 materials, by the presence of complementary textural mesoporosity. A distinctive feature of the present mesoporous metallosilicate molecular sieves is that the ratio of textural to framework-confined mesoporosity can be varied in the range from about 0.2 to 10 by careful selection of the neutral amine template and the reaction conditions. Thus, by varying the textural to framework-confined mesoporosity ratio one can mediate the accessibility of the pore structure of the mesoporous metallosilicate product, depending on the demands of the particular application.

The said compositions can be used as adsorbents, ion-exchangers or catalysts. According to this invention the removal of the template from the reaction product can be achieved by at least four ways: (i) air drying followed by calcination in air or in inert gas at temperature from 300–1000° C. for 30 min to 72 h; (ii) solvent extraction of the templated product; (iii) by vacuum distillation from the product; and (iv) by various combinations of (i) to (iii). The fact that the template can be recycled by non-ionic recovery methods (ii) and (iii) is also a distinctive feature of this invention. Procedure (i) results in the destruction of the template. The separation of the template by extraction or distillation could be followed by air drying and calcination in air or inert gas to remove the final traces of template and to complete the crosslinking of the mesostructure.

After template removal, the said material can be used as an adsorbent for non-polar or polar organic molecules, as a gas drying agent or as a catalyst for cracking, hydrocracking, hydrogenation-dehydrogenation, isomerization or redox reactions involving large organic substrates (kinetic diameters larger than 6 Å)

The new preparation method of the mesoporous catalyst of this invention comprises an inorganic oxide precursor solution containing sources of at least one di-, tri-, tetra-, penta- or hexavalent transition element, or mixture thereof, a source of silicon and a solvent (optional), aging and reacting this solution with a template solution at mild reaction conditions, under stirring, until formation of the desired mesoporous metallosilicate is formed and recovering the mesoporous metallosilicate material. The said template, can be described more particularly as a neutral amine (S°) molecule of formula $R_1R_2R_3N$, wherein N is nitrogen and at least one of $R_1$, $R_2$ and $R_3$ is selected from the group of alkyl of from 6 to 22 carbon atoms or aryl of from 6 to 18 carbon atoms or combination thereof. The remaining R groups are selected from the group consisting of hydrogen or alkyl from 1 to 22 carbon atoms or combination thereof. In addition, a lamellar metal-substituted oxidation catalyst successfully can be synthesized in the presence of neutral diamines (S°—S°) of formula $R_1R_2N$—X—$NR_4 R_5$ wherein X is selected from the group of alkyl, aryl or combination thereof from 1 to 18 carbon atoms and the remaining R groups are selected from the group consisting of hydrogen, alkyl and aryl of from 1 to 18 carbon atoms or a combination thereof.

Preferred reaction mixtures for the typical preparation of the mesoporous metallosilicate compositions of this invention have the following oxide molar ratio ranges:

| Reagents | Useful | Preferred |
| --- | --- | --- |
| S°/SiO$_2$ | 0.01 to 3 | 0.1 to 0.6 |
| KO/SiO$_2$ | 0.005 to 0.5 | 0.01 to 0.2 |
| L$_2$O$_3$/SiO$_2$ | 0.001 to 1 | 0.02 to 0.4 |
| MO$_2$/SiO$_2$ | 0.001 to 0.5 | 0.01 to 0.25 |
| NO$_p$/SiO$_2$ | 0.001 to 0.5 | 0.01 to 0.2 |
| H$_2$O/SiO$_2$ | 10 to 250 | 20 to 150 |
| co-solvent/H$_2$O | 0 to 5 | 0 to 1 | wherein S° is at least one neutral amine or diamine (S°—S°) such as dodecyl amine or 1,12-diaminododecane; K is optional and is at least one divalent element such as Mg, Zn or Cu; L is optional and is at least one trivalent element such as B, Al, Ga, Cr or Fe; M is optional and is at least one tetravalent element different from silicon such as Ti, V, Sn, Ge or Zr; N is optional and is at least one pentavalent or hexavalent element such as V, W or Mo.

The preparation procedures of the said compositions comprise steps as follows:

(i) Preparing a solution of at least one di-, tri-, tetra-, penta- or hexavalent transition metal precursor and neutral silicon precursor in the presence (optional) of hydrolyzing agent and/or co-solvent.

(ii) Aging the inorganic oxide precursors solution under stirring for at least 5 min at a temperature of at least minus 20° C. (aging is optional).

(iii) Preparing a solution of the neutral template in a hydrolyzing agent or in a hydrolyzing agent and co-solvent.

(iv) Reacting the inorganic oxide precursors solution with the template solution by stirring at a temperature from minus 20° C. to plus 100° C.

(v) Aging the resulting reaction mixture under stirring at the desired temperature for at least 30 min.

(vi) Air drying the product or separating the template by either solvent extraction with water or alcohol or a mixture thereof, or by distillation of the templated product. After template removal the product is subjected to calcination to remove trace amounts of template and to complete the crosslinking of the framework.

(vii) Calcining the product at 300 to 1000° C. in air or inert gas for at least 30 min.

Herein said inorganic oxide solutions are prepared from neutral precursors such as alkoxides, inorganic hydrocarbons such as silanes, or inorganic complexes which upon hydrolysis afford a T-OH species. The list of preferred alkoxides include, in particular, magnesium(II) ethoxide, manganese(II) isopropoxide, copper(II) methoxyethoxide, lead(II) isopropoxide, lead(II) tert-butoxide, strontium(II) isopropoxide, zinc(II) isopropoxide, zinc(II) tert-butoxide, aluminum(III) tri-ethoxide, aluminum(III) isopropoxide, aluminum(III) n-, tert- or sec-butoxide, antimony(III) isopropoxide, antimony(III) n-butoxide, chromium(III) isopropoxide, gallium(III) isopropoxide, indium(III) isopropoxide, iron(III) ethoxide, iron(III) tert-butoxide, iron (III) isopropoxide, chromium(IV) tert-butoxide, germanium (IV) ethoxide, germanium(IV) isopropoxide, tetramethyl orthosilicate, tetraethyl orthosilicate (TEOS), tetrapropyl orthosilicate, tetrabutyl orthosilicate, tetrahexyl orthosilicate, $H[OSi(OC_2H_5)_2]_nOH$ where n=4–6, RSi(OR) $_3$, tin(IV) isopropoxide, tetraethyl orthotitanate, tetrapropyl orthotitanate, tetraisopropyl orthotitanate (TIPOT), tetrabutyl orthotitanate, tetraoctadecyl orthotitanate, zirconium(IV) n-propoxide, zirconium(IV) isopropoxide, zirconium(IV) tert-butoxide, molybdenum(V) isopropoxide, niobium(V) ethoxide, tungsten(VI) ethoxide, tungsten(VI) isopropoxide, vanadium(V) triisopropoxide oxide or mixtures thereof. Also a variety of a neutral colloidal inorganic oxide precursor solutions or inorganic oxide gels also can be used to prepare the compositions of the present invention. For example, potential sources of a neutral silica include a variety of commercially available fumed silicas or silica gels.

Said co-solvent (optional) is selected from the group of normal or isomerized alcohols having 1 to 12 carbon atoms and at least one OH group, such as methanol, ethanol, propanol, buthanol, hexanol, octanol, dodecanol. More preferably, said co-solvent is an ethanol, propanol, 2-propanol or mixture thereof. Those skilled in the art will know that polyols in which more than one OH group is present also can be used as a co-solvent.

The said aging of the substituted inorganic oxide precursor solution is optional and preferably performed at 60–80° C. for 3–4 h.

The said template is a neutral primary, secondary or tertiary amine or polyamine or mixture thereof, preferably a primary amine or diamine, having at least one alkyl chain of from 6 to 22 carbon atoms or mixtures thereof.

Said reacting of the inorganic oxide precursors solution and template solution is preferably carried out at 20 to 45° C. by random order of reagent addition, more preferably by adding the inorganic oxide precursors solution to the template solution under vigorous stirring. More specifically said reacting is performed by H-bonding between neutral inorganic oxide precursors and a neutral template, followed by further hydrolysis and crosslinking of $TO_4$ units at mild reaction conditions. This H-bonding most likely occurs generally between any T-OH or T-proton donor compound and the lone pair of electrons on the central atom of the head group of the organic template.

The said aging of the reaction mixture is accomplished preferably for 0.5–24 h, more preferably from 12 to 18 h.

Said calcinating is performed by heating in an oven at a temperature preferably from 300–650° C. for 4 h.

Said solvent extraction was preferably accomplished by mixing of the as-synthesized templated product with ethanol in a ratio of from 1 to 200 (w/w) at 45 to 80° C. for 30 min. The product was then filtered and washed with another portion of ethanol. The above washing procedure was repeated twice and the product was air dried in open air or in oven at 80° C.

The preparation of metal-substituted MCM-41 molecular sieves was accomplished by novel S$^+$X$^-$I$^+$ (Pathway 3) at mild reaction conditions. This preparation comprises similar reaction steps and molar ratios of reagents as outlined for the neutral HMS synthesis. However, a cationic quaternary ammonium template (S°) and significant amounts of acid (mediating X$^-$ anions) were used instead of the neutral template and the neutral conditions. This differs from all prior art teachings for metal ion substitutions in mesoporous silicas. All previously reported metal-substituted MCM-41 materials were prepared by a hydrothermal treatment using Pathway 1 (S$^+$I$^-$) templating. This teaching is also quite different from all prior art catalytic applications of transition metal-substituted MCM-41 materials since the molecules subjected to catalytic peroxide oxidation were nonaromatic and smaller that the 2,6-di-tert-butyl phenol substrate oxidized in this invention (see Corma et al. *J. Chem. Soc. Chem. Commun.*, 147–148 (1994)).

The catalytic oxidation of the large organic substrates of the present invention can be performed over the above transition metal-substituted mesoporous molecular sieves using peroxides such as hydrogen peroxide or tertbutyl peroxide as oxygen donors or oxidants. Hydrogen peroxide is the preferred oxidant because it produces only water upon its decomposition and does not pollute the environment. Yet another important advantage over the other peroxide oxidants is that hydrogen peroxide contains about 47% of active oxygen useful for oxidation whereas the others, such as tertbutyl peroxide, afford only about 18% active oxygen. By analogy with TS-1 the mechanism by which our mesoporous metallosilicates act as an oxidation catalyst could involve in the initial stage the formation of surface peroxocomplex between the H$_2$O$_2$ and the site isolated transition metal species:

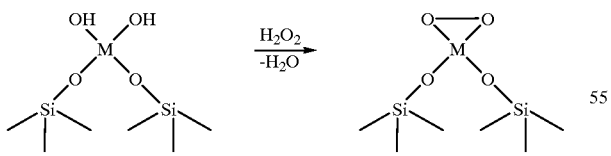

In the next stage this surface peroxide complex, that is located within the uniform mesopores of our metallosilicate, most likely donates oxygen to the adsorbed large organic substrate assuming again its initial hydroxylated state. Specifically, the reaction of 2,6-di-tert-butylphenol (2,6-DTBP) to the corresponding quinone can be expressed as follows:

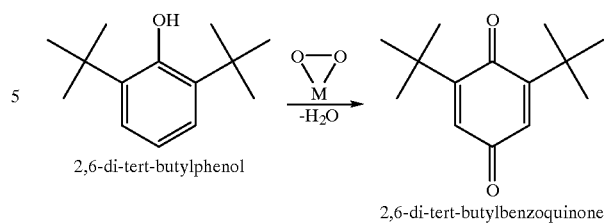

2,6-di-tert-butylphenol 2,6-di-tert-butylbenzoquinone

The unusual catalytic activity and selectivity of our mesoporous metallosilicate molecular sieves for peroxide oxidations of large aromatic substrates can be explained by the presence of site isolated Si—O—T—O—Si species within the uniform mesopores capable of oxygen transfer via peroxocomplexes to substrates with strictly limited kinetic diameters. Since our mesoporous metallosilicates are in general hydrophobic and some of the large aromatics are nonpolar, the presence of solvent in the reaction mixture is essential in order to ensure miscibility with the H$_2$O$_2$. A large number of compounds such as water, methanol, ethanol, acetonitrile, acetone and butanol can successfully be used as a solvents for our oxidation reactions. The oxidation reactions of this invention can be performed under static conditions or vigorous stirring in a glass flask or autoclave at temperature from 0 to 100° C. for at least 20 min using catalyst to substrate weight ratio of at least 0.001, H$_2$O$_2$ to substrate molar ratio of at least 0.05 and solvent to substrate molar ratio in the range of 0 to 500. In particular, the oxidation of 2,6-DTBP was carried out at reflux temperature (62° C.) in a glass flask for 2 h using 0.5 and 5 mmol of 2,6-DTBP, substrate to solvent (acetone) molar ratios of 1:270 and 1:27, respectively, a catalyst to substrate ratio of 1:1 and 1:10 (w/w), and adequate amount of 30 wt % aqueous H$_2$O$_2$ to give substrate to H$_2$O$_2$ molar ratios of 1:1, 1:2, and 1:6. The hydroxylation of benzene was carried out at 72° C. for 24 h using 100 mmol of benzene as substrate, catalyst to substrate ratio of 1:372 (w/w) and substrate to hydrogen peroxide molar ratio of 3:1. This reaction was carried out in the absence of solvent.

The outstanding features of the present invention are:

(i) The use of neutral template assemblies, particularly amines (S°) or diamines (S°13 S°), to assemble the metal-substituted mesoporous hexagonal, hexagonal-like or lamellar framework;

(ii) The use of neutral inorganic oxide precursors (I°) such as alkoxides, inorganic complexes or inorganic oxide sols and gels as sources of substituting metal (M) and silica.

(iii) The aging of the substituted inorganic oxide precursor solution at 60–80° C. for 1–4 h in order to obtain polymerized -M-O-T-species.

(iv) The use of hydrogen bonding as a driving force for the neutral S°I° assembly process between the neutral template and neutral inorganic oxide precursor species;

(v) The use of mild reaction conditions to prepare the templated mesoporous molecular sieve product;

(vi) The recovery and recycling of the neutral template by a new separation art involving simple non-ionic solvent extraction or distillation from the product.

(vii) The use of S$^+$X$^-$I$^+$ templating route and mild reaction conditions to prepare non-layered, hexagonal or mesoporous transition metal-substituted MCM-41 materials.

(viii) The use of these new and useful mesoporous metallosilicate molecular sieves as oxidation catalysts of aromatic compounds that are too large (kinetic diameters>6 Å) to access the pores of the conventional microporous transition metal-substituted molecular sieves.

The metal-substituted mesoporous molecular sieves of the present invention may be combined with other zeolites or clays or inorganic oxides or organic polymers or mixture thereof, in order to prepare adsorbents, ion-exchangers, catalysts, catalytic carriers or composite membranes with high thermal and mechanical resistance. Due to their highly accessible mesopore framework these catalysts can be used in variety of conversion reactions involving large organic substrates (kinetic diameter>6 Å) such as catalytic cracking, hydrocracking, reforming, isomerization, dealkylation or oxidation in the presence or absence of $H_2O_2$ or $O_2$ or mixture thereof.

The following specific examples are intended to be illustrative of the present invention, but are not intended to limit the invention in any way.

LIST OF THE ABBREVIATIONS

TS-1—microporous titanium substituted silicate molecular sieve with MFI topology (analogous to ZSM-5).
TS-2—microporous titanium substituted silicate molecular sieve with MEL topology (analogous to ZSM-11).
Ti-ZSM-48—microporous titanium substituted silicate molecular sieve with ZSM-48 topology.
ETS-10—Engelhard Corporation titanosilicate molecular sieve (microporous) with titanium in tetrahedral and octahedral coordination.
VS-1—microporous vanadium substituted silicate molecular sieve with MFI topology.
VS-2—microporous vanadium substituted silicate molecular sieve with MEL topology.
M41S—broad family of mesoporous siliva based molecular sieves with lamellar, hexagonal or cubic structure.
MCM-41—Mobil Composition of Matter possessing long range hexagonal order (a member of the M41S family).
Ti-MCM-41—titanium-substituted analog of MCM-41.
HMS—hexagonal or hexagonal-like mesoporous molecular sieve.
Ti-HMS—titanium-substituted mesoporous molecular sieve possessing hexagonal or hexagonal-like order.
V-HMS—vanadium-substituted mesoporous molecular sieve possessing hexagonal or hexagonal-like order.
Cr-HMS—chromium-substituted mesoporous molecular sieve possessing hexagonal or hexagonal-like order.
PLMS—pillared lamellar mesoporous silicate preparared by direct neutral templating method.
LDH—layered double hydroxide.
TEOS—tetraethyl orthosilicate: $Si(OC_2H_5)_4$.
TEOT—tetraehyl orthotitanate: $Ti(OC_2H_5)_4$.
TIPOT—tetraisopropyl orthotitanate: $Ti[OCH(CH_3)_2]_4$.
TMAOH—tetramethylammonium hydroxide: $(CH_3)_4NOH$.
TEAOH—tetraethylammonium hydroxide: $(C_2H_5)_4NOH$.
TPAOH—tetrapropylammonium hydroxide: $(C_3H_7)_4NOH$.
TPA$^+$—tetrapropylammonium cation: $(C_3H_7)_4N^+$.
TBA$^+$—tetrabutylammonium cation: $(C_4H_9)_4N^+$.
CTMABr—cetyltrimethylammonium bromide: $[C_{16}H_{33}(CH_3)_3N]Br$.
DDA—dodecylamine: $C_{12}H_{25}NH_2$.
i-PrOH—isopropyl alcohol: $CH_3CHOH$.
EtOH—ethyl alcohol: $C_2H_5OH$.
2,6-DTBP—2,6-di-tert-butylphenol: $[(CH_3)_3C]_2C_6H_3OH$.
2,6-DTBBQ—2,6-di-tert-butylbenzoquinone: $[(CH_3)_3C]_2C_6H_2O_2$.
3,3,5,5-TTB-4,4'-DPQ—3,3,5,5-tetra-tert-butyl-4,4'-diphenoquinone.
H-bonding—hydrogen bonding.
XRD—X-ray diffraction pattern.
SEM—scanning electron microscopy.
TEM—transmission electron microscopy.
$S_{BET}$—specific surface area in $m^2/g$ obtained by the linear part of the Brunauer-Emmett-Teller equation.
$V_t$—total volume of pores in $cm^3/g$.
$P_i/P_o$—relative pressure. $P_i$ is the equilibrium pressure of the adsorbate and $P_o$ is the saturation pressure of the adsorbate at the temperature of the adsorbent, volume adsorbed is at standard temperature and pressure.
FID—flame ionization detector.
HK—Horvath-Kawazoe pore size distribution.

Comparative Example 1

For comparison purposes, a microporous TS-1 molecular sieve was prepared as described by Thangaraj et al., *Zeolites*, 12, 943–950 (1992). The product was filtered, washed and calcined in air at 650° C. for 4 h prior all measurements. The material exhibited a XRD diffraction pattern typical for TS-1 microporous molecular sieves. The specific surface area (denoted $S_{BET}$) of the crystalline product of this example is 398 $m^2/g$ and the $V_t$–0.61 cc/g. The pore volume corresponding to the framework-confined micropores is ≈0.2 cc/g and the volume of textural mesopores is 0.41 cc/g. The ratio of textural mesoporosity to framework microporosity here is 2.0. The size of framework-confined uniform micropores is approximately 5.5 Å.

Comparative Example 2

This example was chosen to illustrate the prior art hydrothermal synthesis of Ti-MCM-41 molecular sieve using $S^+I^{-31}$ (Pathway 1) templating route. The preparation procedure was generally that described by Mobil researchers in Beck et al., *Chem. Mater.*, 6, 1816–1821 (1994) but the source of silica was modified in order to avoid the unwanted Na and the appropriate amount of $Ti(i-PrO)_4$ was added to obtain the Ti-substituted derivative. For a typical preparation 36.2 g of 30 wt % colloidal silica (LUDOX@ SM-30) was mixed with 16.3 g of 25 wt % solution of TMAOH (Aldrich) and the resulting mixture was stirred for approximately 30 min. A separate solution of 33.5 g of cetyltrimethylammonium bromide (CTMABr) in 199 g of deionized water and 11.2 g of 10% sulfuric acid was also prepared under vigorous stirring. The mixture was heated gently until a homogeneous solution of the quaternary ammonium template was obtained. Both solutions were mixed and the appropriate amount of $Ti(i-PrO)_4$ was added (0.51 g-portion) to prepare a material with $TiO_2/SiO_2$ ratio of 0.01). The obtained reaction mixture was stirred at ambient temperature for 30 min, then a 1.9 g-portion of 50 wt % sulfuric acid was added and the mixture was transferred to an autoclave and heated at 100° C. for 6 d. The Ti-MCM-41 product was filtered, washed and calcined in air at 650° C. for 4 h. The X-ray diffraction pattern of the calcined sample as well as its adsorption properties are typical for the prior art MCM-41 samples prepared by hydrothermal treatment and an $S^+I^-$ templating pathway.

EXAMPLES 3–8

The following examples demonstrate the preparation of a Ti-substituted hexagonal or hexagonal-like mesoporous molecular sieves (denoted Ti-HMS) using our $S°I°$ templating method. For this particular examples 13.66 g of TEOS were added to 25 ml of EtOH and stirred. A solution of 0.22, 0.45, 1.12, 1.6 or 2.25 g TIPOT in 10 ml isopropyl alcohol (i-PrOH) was quickly added to the TEOS solution under vigorous stirring in order to obtain 1, 2, 5, 7 and 10 mol % Ti-substituted material, respectively. The resulting clear mixture was then heated and stirred at 65–80° C. for 3 h to obtain the —Ti—O—Si— polymerized species (this aging is optional).

A separate solution of 3.27 g of dodecylamine (DDA) in 25 ml of water was prepared under stirring. The clear —Ti—O—Si— solution was aged and then added at once to the above template solution. The resulting mixture was stirred and aged at ambient temperature for 18 h in order to prepare the Ti-substituted hexagonal mesoporous silicas (1–10% Ti-HMS). The molar composition of the initial reaction mixture per mole of $SiO_2$ was:

0.01, 0.02, 0.05, 0.07 or 0.1 moles $TiO_2$ (EXAMPLES 3–8, respectively)

0.27 moles $C_nH_{2n+1}NH_2$ 21.2 moles $H_2O$ 6.54 moles EtOH 1.99 moles i-PrOH The products were air dried and calcined in air at 650° C. for 4 h. The powder X-ray diffraction patterns were measured on Rigaku Rotaflex diffractometer equipped with a rotating anode and using Cu—$K_a$ radiation. The scattering domain size was determined from the line width of the $d_{100}$ x-ray reflection. The $N_2$ adsorption-desorption isotherms were measured at −195° C. on a Coulter Omnisorp 360CX Sorptometer using a continuous adsorption procedure. Before measurement, samples were evacuated overnight at 150° C. and $10^{-6}$ torr. The repeat distance ($a_o$) between pore centers of the hexagonal structure is calculated from the XRD data with the formula $a_o=2d_{100}/\sqrt{3}$. The framework-confined mesopore size (HK pore size) was determined by Horvath-Kawazoe (HK) analysis of the $N_2$ adsorption isotherms. The framework wall thickness is determined by subtracting the HK mesopore size from the repeat distance between pore centers.

Figure 2:
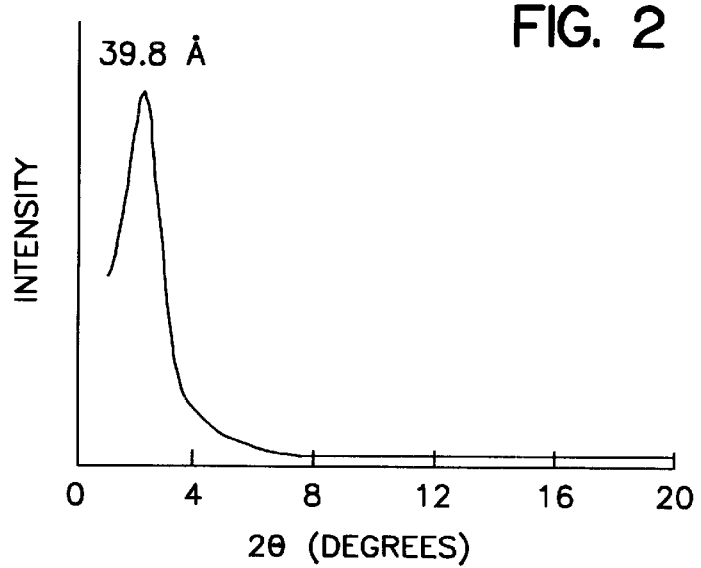
FIG. 2 is an X-ray powder diffraction pattern of the product of Example 3.
Figure 3:
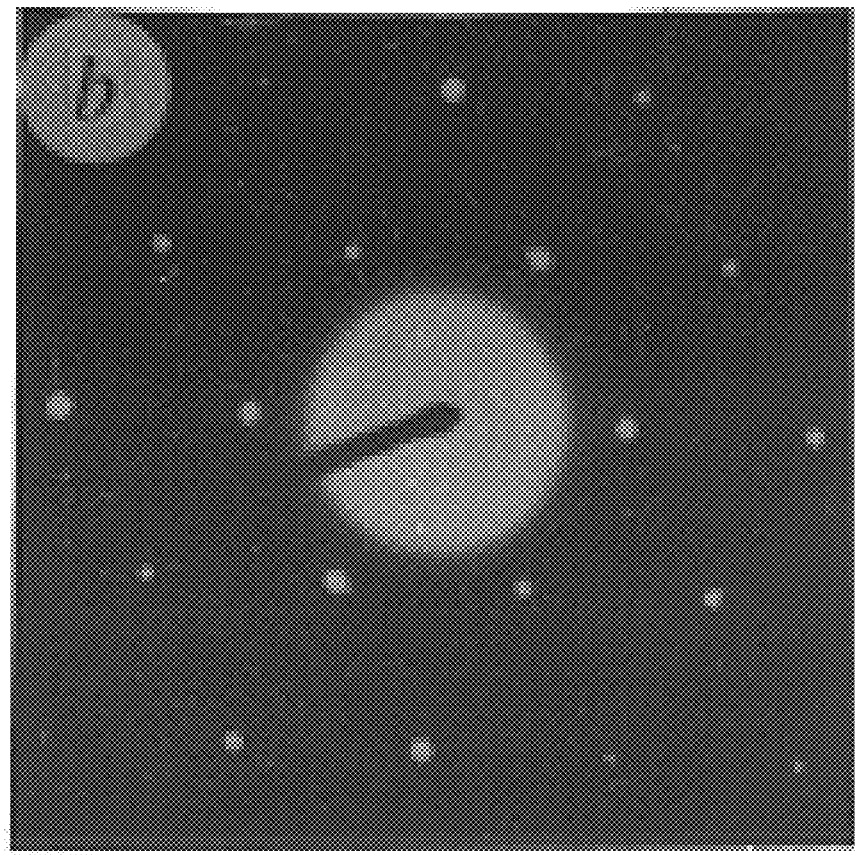
FIG. 3 is an electron diffraction pattern of the product of Example 3.

All X-ray diffraction patterns of the calcined samples exhibit single $d_{100}$ reflections centered at d-spacings equal to or greater than 36 Å along with a more or less pronounced diffuse scattering at d-spacings where the remaining hk0 reflections (110, 200 and 210) of the hexagonal phase are expected. The X-ray diffraction pattern of the calcined 1% Ti-HMS is shown in FIG. 2. It exhibits a strong relative intensity reflection at 40±1.0 Å d-spacing and a diffuse scattering centered at ≈18.0±2.0 Å. Higher order Bragg reflections of the hexagonal structure are not resolved. However, the electron diffraction pattern of this sample, presented as FIG. 3, reveals typical hexagonal arrangement of the diffraction maxima similar to that observed for pure MCM-41 materials by prior art (U.S. Pat. No. 5,098,684). The scattering domain size of 1% Ti-HMS, calculated from the line width of the $d_{100}$ reflection is only about 170 Å. In general the scattering domain size of the 1–10% Ti-HMS samples does not exceed 250 Å. Thus, the diffuse scattering at ≈18 Å could be attributed to broadening of the remaining hk0 hexagonal reflections due to the small domain size effects.

EXAMPLE 9

Figure 4:
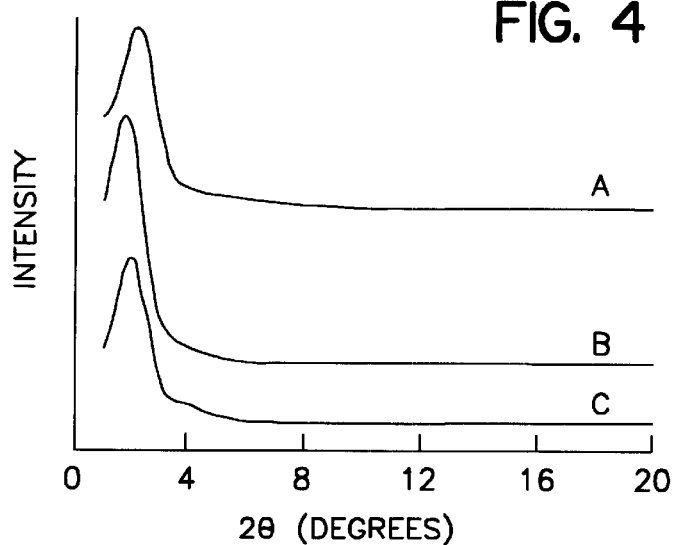
FIG. 4 are X-ray diffraction patterns of Example 9: (A) calcined Product A; (B) ethanol extracted Product B and (C) ethanol extracted and calcined Product C.

The following example was chosen to exemplify the neutral template recovery art of the present invention. For this particular example, the template removal from the air-dried material of EXAMPLE 3 was accomplished either by calcination in air at 650° C. for 4 h (Product A) or by simple solvent extraction (Product B). The template extraction was carried out by mixing 1 g of the air dried product with 100 ml of EtOH at 45 to 80° C. for 30 min. The product was then filtered and washed with another portion of EtOH (100 ml). The above washing procedure was repeated twice and the product was air dried in oven at 80° C. Significantly, the X-ray diffraction pattern of the EtOH washed product B exhibits a $d_{100}$ reflection at 48±1 Å that is four times more intense than the calcined Product B (see FIG. 4). In addition, a well expressed diffuse scattering at 22±2 Å is also observed. The ethanol extracted sample (Product B) does not decompose and is thermally stable even after prolonged calcination at elevated temperatures (Product C). This is evidenced by the retention of the d-spacing (41 Å) and the accompanying diffuse scattering after calcination in air at 650° C. for 4 hours (see FIG. 4C). Thus, the removal of the neutral template by the solvent extraction method of the present invention tends to preserve the crystallinity of the product, whereas local heating during calcination might cause some degradation of the mesoporous framework. The extracted organic template in the form of EtOH solution can be recycled and reused after simple concentration of the solution.

Figure 5:
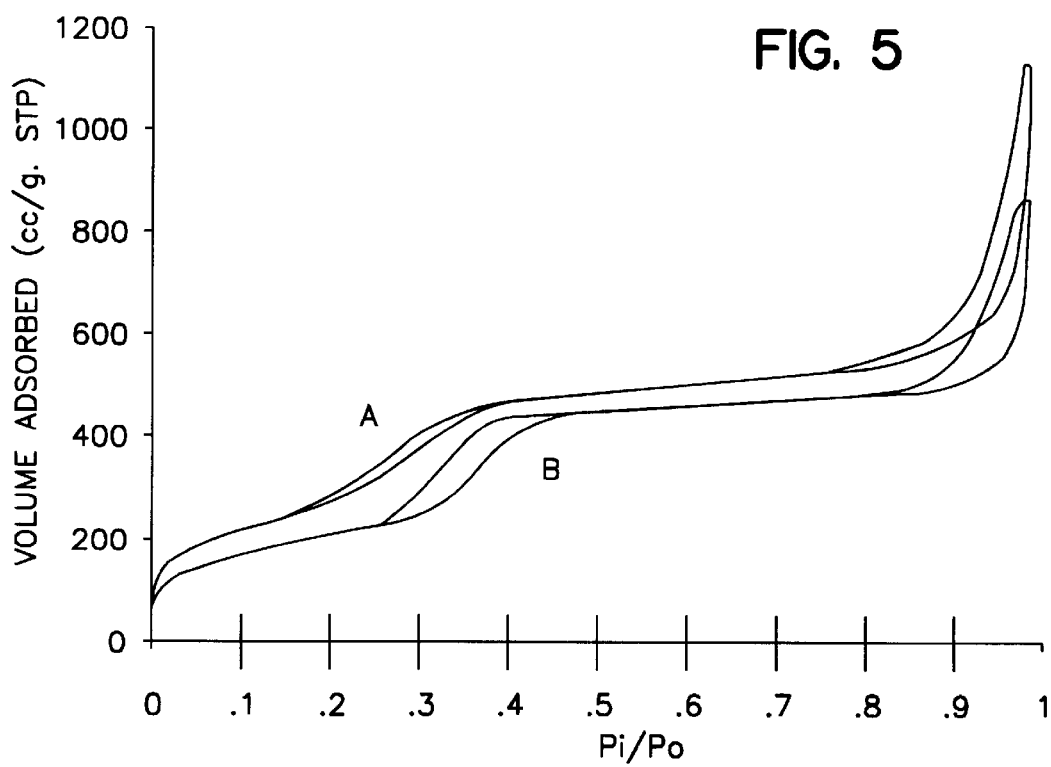
FIG. 5 is a $N_2$ adsorption-desorption isotherms for: (curve A) the calcined Product A of Example 9 and (curve B) for the ethanol extracted Product B of Example 9.
Figure 6:
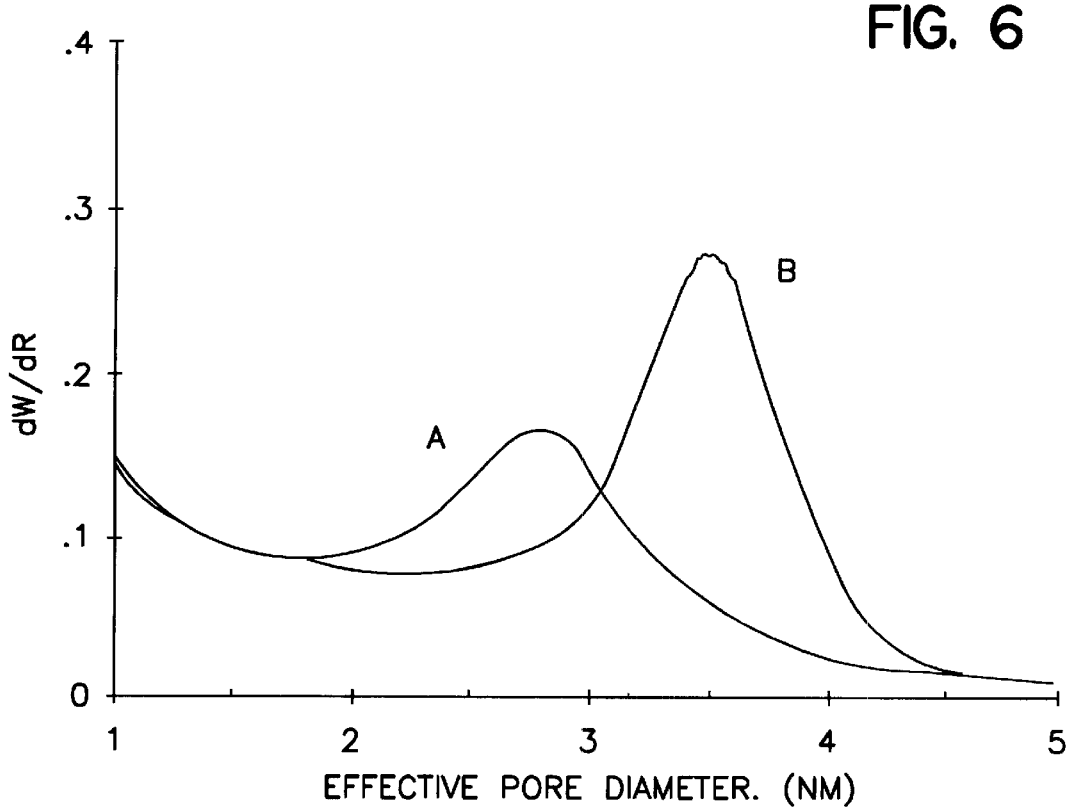
FIG. 6 are Horvath-Kawazoe framework-confined mesopore size distribution curves for (A) calcined Product A and (B) ethanol-extracted Product B of Example 9.

The $N_2$ adsorption-desorption isotherm for the calcined Product A (1% Ti-HMS sample) is shown in FIG. 5A. Included for comparison is the isotherm for the ethanol extracted Product B (FIG. 5B). Both $N_2$ adsorption-desorption isotherms exhibit similar complementary framework-confined and textural mesoporosity as evidenced by the presence of two well-defined, separate hysteresis loops. The $S_{BET}$ of both samples are also similar—1046 and 803 $m^2/g$, respectively. The total pore volume of the calcined Product A is 1.75 cc/g. The pore volume corresponding to the uniform framework mesopores is 0.71 cc/g and the volume of the textural mesopores is 1.04 cc/g. The ratio of textural to framework mesoporosity here is 1.46. The total pore volume of the EtOH extracted Product B is 1.31 cc/g, the volume of framework-confined mesopores is 0.69 cc/g and that of the textural mesopores is 0.62 cc/g. The corresponding ratio of textural to framework-confined mesoporosity for this sample is 0.9. This suggests that ethanol extraction effectively removes the neutral template from the framework-confined mesopores of our S° I° Ti-HMS, while at the same time preserving the crystallinity of the catalyst and balancing the amount of textural and framework-confined mesoporosity. The corresponding Horvath-Kawazoe pore size distribution curves for both samples are presented in FIG. 6. The size of framework-confined uniform mesopores of the calcined Product A is 28 and that of the EtOH extracted Product B is 36 Å. The larger uniform pore size of the EtOH extracted catalyst could be again attributed to the preservation of the crystallinity upon EtOH extraction, whereas the smaller pore size of the calcined material is probably due to partial collapse of the mesoporous framework during calcination.

The pure HMS samples, prepared by neutral templating with primary amines of different alkyl-chain length, exhibit consistently larger framework wall thickness (equal to or larger than 17 Å) than that of MCM-41 materials prepared by electrostatic templating (equal to or less than 12 Å). In accord with these observations the framework wall thickness of our calcined Ti-HMS (Product A) and ethanol extracted (Product B) also are much larger (18 and 19 Å) relative to that for the calcined Ti-MCM-41 material with the same Ti loading (12 Å).

EXAMPLE 10

The hereafter described procedure demonstrates that our Ti-HMS mesoporous molecular sieve can be successfully prepared by acid catalyzed hydrolysis of the inorganic precursors in the presence of partially protonated primary amine ($S^°/S^+$). This procedure was originally reported by us in Pinnavaia et al., Nature, 368, 321–323 (1994). It should be noted that the molar ratio of $S^°:S^+$ for a successful preparation of Ti-HMS should be in the range of 1:0 to 1:1. For this particular preparation 13.66 g of TEOS were added to 25 ml of EtOH and stirred. A solution of 0.185 g TIPOT in 5 ml isopropyl alcohol (i-PrOH) was quickly added to the TEOS solution under vigorous stirring. The resulting clear solution was then heated and stirred at 65–80° C. for 3 h to obtain the —Ti—O—Si— polymerized species.

A separate solution of 3.27 g of dodecylamine (DDA) in 30 ml of water and 13 ml of 0.1 M HCl was prepared under stirring. The clear Ti—O—Si solution was aged and then added at once to the above template solution. The resulting mixture was stirred and aged at ambient temperature for 16 h in order to prepare the Ti-HMS crystalline product. The molar composition of the reaction mixture per mole of $SiO_2$ was:

0.01 moles TIPOT
0.27 $C_nH_{2n+1}NH_2$
0.02 moles HCl
36.3 moles $H_2O$
6.5 moles EtOH
1.0 moles i-PrOH The product was air dried and calcined at 650° C. for 4 h. The X-ray diffraction pattern was nearly identical to that of Example 3. This sample exhibited strong XRD peak at 38±1.0 Å d-spacing and a diffuse scattering centered at ≈17.0±2.0 Å. The framework wall thickness of this product is 15 Å and the scattering domain size was found to be <250 Å. The electron diffraction pattern of this product and the corresponding $N_2$ adsorption-desorption isotherm were similar to that observed for Example 3. The $S_{BET}$ of the crystalline product of this example is 1031 $m^2/g$ and the $V_t$-1.79 cc/g. The pore volume corresponding to the framework-confined mesopores is 0.68 cc/g and the volume of textural mesopores is 1.11 cc/g. The ratio of textural to framework mesoporosity here is 1.46. The size of framework-confined uniform pores of the product as determined from Horvath-Kawazoe pore size distribution curve is 29 Å. The corresponding framework wall thickness of this product was found to be 15 Å.

EXAMPLE 11

The preparation procedure employed here was identical to that of Example 3 except that the order of addition of solutions was changed. In contrast to Example 3 the template here was first mixed with the —Ti—O—Si— solution under vigorous stirring. The appropriate amount of water was then added at once to the above clear template/—Ti—O—Si— solution. The calcined product exhibits X-ray d-spacing of 42.5±2.0 Å and diffuse scattering centered at 18.0±2.0 Å. The framework wall thickness is 22 Å and the corresponding elementary particle size of the product, as judged by TEM, was found to be <300 Å. The $S_{BET}$ of this product is 968 $m^2/g$ and the $V_t$ is 1.82 cc/g. The pore volume corresponding to the uniform framework-confined mesopores is 0.45 cc/g and the volume of textural mesopores was 1.37 cc/g. The textural to framework-confined mesoporosity ratio for this sample was found to be 3.12. The pore size of the product as determined by Horvath-Kawazoe method is 27 Å.

EXAMPLE 12

This example illustrates the effect of the neutral template alkyl chain length on the 2,6 DTBP oxidation activity of Ti-HMS prepared by $S^°I^°$ templating pathway. All the Ti-HMS samples shown in TABLE I were prepared using primary amines with different alkyl chain length following the method described in example 3 with only minor modifications. In the present preparation, the molar composition of the reaction mixture per mole of $SiO_2$ was as follows:

0.025 moles $TiO_2$
0.3 moles $C_nH_{2n+1}NH_2$ (where $C_n=C_8$, $C_{12}$, $C_{16}$ or $C_{18}$)
21.0 moles water
6.5 moles EtOH
1.95 moles i-PrOH.

The products were air-dried and calcined at 650° C. for 4 h prior all catalytic tests. The effect of template alkyl chain length on the catalytic activity and selectivity was evaluated using peroxide oxidation of 2,6-DTBP to the corresponding mono- and binuclear quinones. The reaction was carried out by refluxing in a glass flask at 62° C. for 20 h using 5 mmol 2,6-DTBP, substrate to solvent (acetone) molar ratio of 1:27, a catalyst to substrate ratio of 1:10 (w/w), and a substrate to $H_2O_2$ molar ratio of 1:3. The corresponding conversions are summarized in TABLE II. The quinone yield is defined as the total quinone produced per substrate feed. The total quinone selectivity was calculated as a ratio of quinone yield versus percent conversion.

TABLE I

Properties of the Calcined 2.5 mol % Ti-HMS Catalysts Prepared by Neutral $S^°$ $I^°$ Templating as a Function of the Template Alkyl Chain Length.

| Template alkyl chain length | $d_{100}$ (Å) | $a_o$ (Å) | HK pore size (Å) | Wall thickness (Å) |
|---|---|---|---|---|
| $C_8$ | 34 | 39 | 15 | 24 |
| $C_{12}$ | 36 | 41 | 22 | 19 |
| $C_{18}$ | 44 | 51 | 40 | 11 |

TABLE II

Effect of the Template Alkyl Chain Length on the Catalytic Activity of 2.5 mol % Ti-HMS Prepared by $S^°$ $I^°$ Templating for Peroxide Oxidation of 2,6-DTBP.

| Template alkyl chain length | Conversion (%) | Total Quinone Yield (%) | Quinone Distribution Mono:Dimer |
|---|---|---|---|
| $C_8$ | 42 | 32 | 49:51 |
| $C_{12}$ | 77 | 63 | 36:64 |
| $C_{18}$ | 76 | 71 | 31:69 |

The following trends are evident by comparing the data presented in the TABLES I and II: as the alkyl chain length of the template increases (i) the framework-confined mesopore size increases; (ii) the 2,6-DTBP conversion also increases; (iii) the corresponding quinone yield increases; (iv) the selectivity to the monomer decreases and (v) the selectivity to dimer increases. Therefore, one skilled in the art could improve the selectivity toward monomer by using shorter reaction time and shorter alkyl chain length and vice versa. This particular teaching is not apparent from any prior art teachings.

EXAMPLES 13–15

This examples illustrate the ambient temperature preparation of Ti-MCM-41 as originally reported by us in Pinnavaia et al., Nature, 368, 321–323 (1994). This differs from all prior art teachings since all known transition metal-substituted MCM-41 materials were prepared by a hydrothermal treatment using $S^+I^-$ templating (Pathway 1).

For these particular examples 13.66 g-portions of TEOS were added to 25 ml of EtOH and stirred. A solution of 0.185, 0.37 or 1.85 g TIPOT in 10 ml isopropyl alcohol (i-PrOH) was quickly added to the TEOS solutions under vigorous stirring in order to obtain 1, 2 and 10% Ti-substituted material, respectively. The resulting clear mixture was then heated and stirred at 65–80° C. for 3 h to obtain the —Ti—O—Si— polymerized species (aging and heating is optional).

Figure 7:
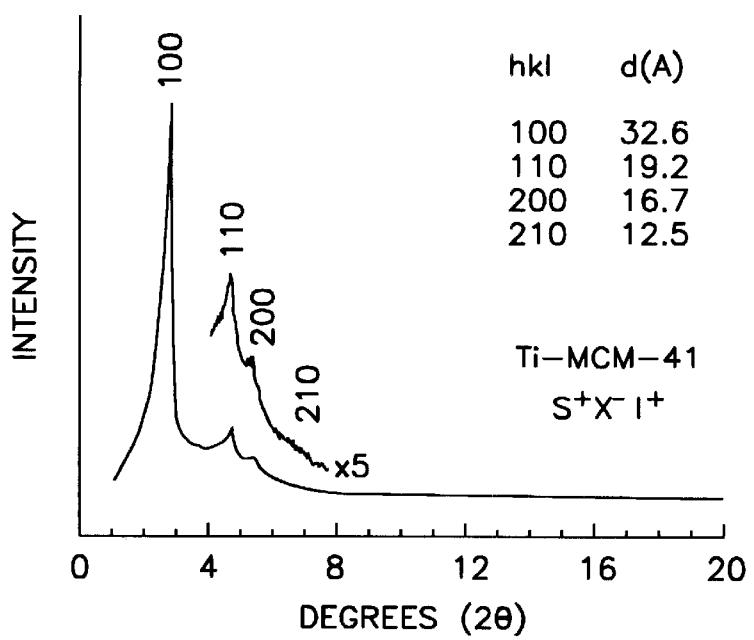
FIG. 7 is an X-ray diffraction pattern of the product of Example 13.
Figure 8:
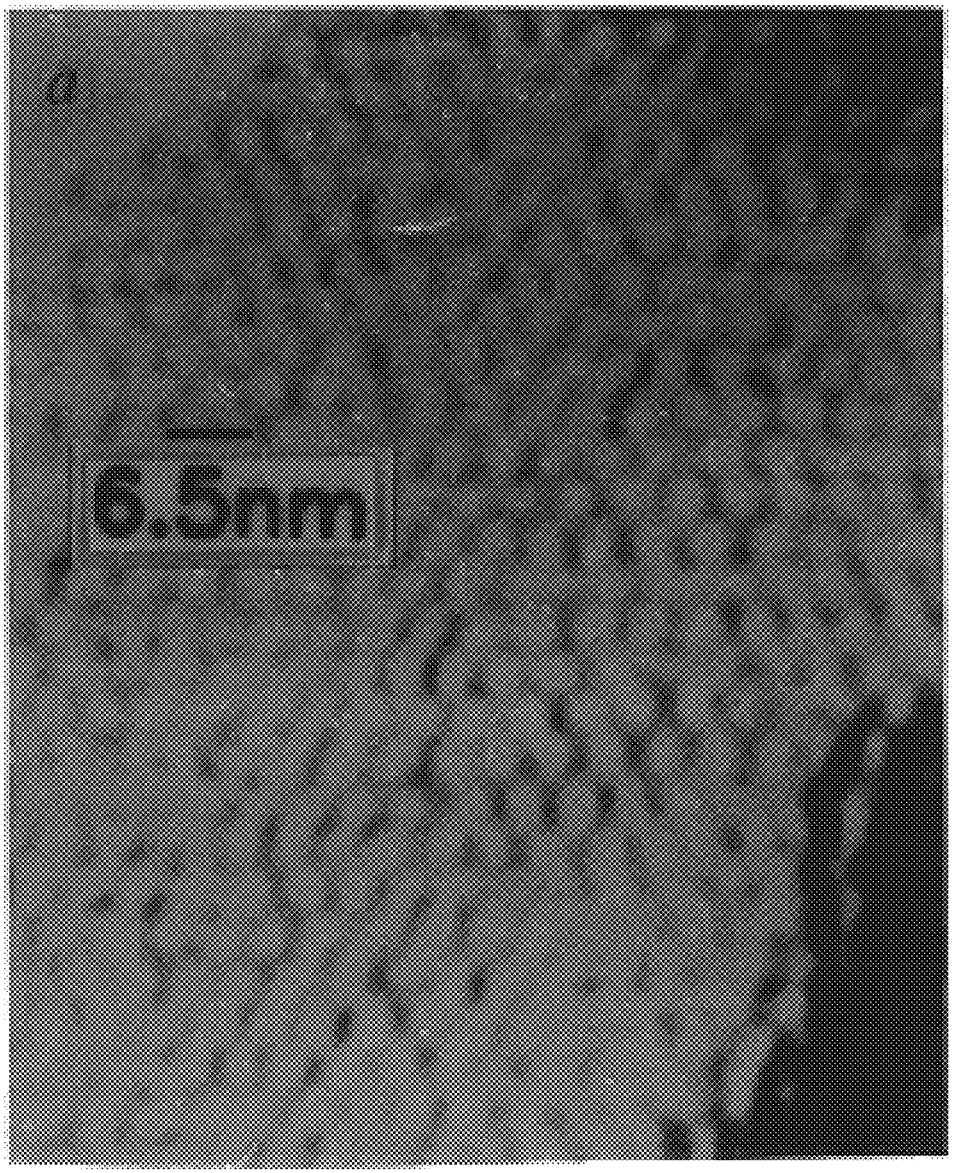
FIG. 8 is a TEM lattice image of thin section of the calcined product of Example 13.
Figure 9:
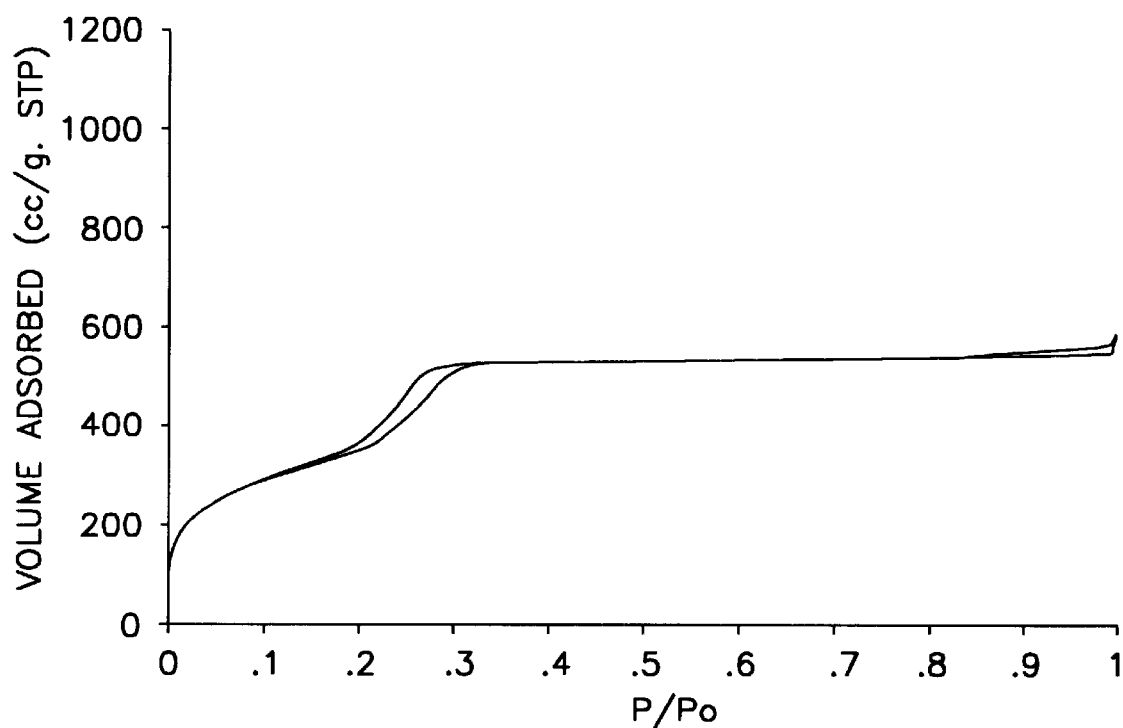
FIG. 9 is a N adsorption-desorption isotherm of the calcined product of Example 13.

The solution of th e template was obtained by dissolving 4.9 g of hexadecyltrimethylammonium bromide in 174 ml of deionized water and 27 ml of 2.5 M HCl. The aged clear —T—O—Si— solution was then added to the above template solution under vigorous stirring. The reaction mixture had the following composition per mole of $SiO_2$:

0.01, 0.02 or 0.03 moles TIPOT 0.2 moles $C_nH_{2n+1}N(CH_3)_3Br$ 1.0 moles HCl 150 moles $H_2O$ 6.5 moles EtOH 2.0 moles i-PrOH The resulting mixtures were aged at ambient temperature for 18 h in order to prepare Ti-substituted MCM-41 materials with 1, 2 and 10% nominal Ti loading. The X-ray diffraction pattern of the 1% Ti-MCM-41 (Example 13) is presented in FIG. 7. It is obvious that this material exhibits typical MCM-41 diffraction pattern. The pattern is characterized by a strong $d_{100}$ reflection at 33±1.0 Å, but owing to the long range hexagonal order weaker 110, 200, and 210 reflections are observed at 2θ range from 4.0 to 7.0. The scattering domain size of this material is much larger that observed for Ti-HMS (940 Å). In addition, the corresponding framework wall thickness of this material is much smaller relative to the Ti-HMS sample (only about 12 Å). The framework-confined uniform mesopores of this Ti-MCM-41 are clearly evident from the TEM lattice image presented in FIG. 8. The $N_2$adsorption-desorption isotherm of this sample is nearly identical to that reported for prior art $S^+I^-$ templated MCM-41 (FIG. 9). The isotherm is characterized by a hysteresis loop at Pi/Po range 0.18 to 0.33 (corresponding to capillary condensation in framework-confined mesopores) and the complete lack of textural mesoporosity. This is evidenced by the absence of a hysteresis loop at Pi/Po>0.4. The $S_{BET}$ for this example is 1345 $m^2$/g and the total pore volume $V_t$ was just about 0.72 cc/g. The volume corresponding to the framework-confined mesopores is 0.69 cc/g and that for the textural mesoporosity only about 0.03 cc/g. Therefore the ratio of textural to framework-confined mesopores for this sample is approximately zero.

EXAMPLE 16

The exceptional catalytic activity of our Ti-HMS and Ti-MCM-41 molecular sieves in comparison to prior art TS-1 in the peroxide oxidation of very large aromatic substrates (kinetic diameter of approximately 10 Å) is illustrated by the conversion of 2,6-di-tert-butylphenol (2,6-DTBP) to the corresponding quinones. The catalytic reaction was carried out at reflux temperature (62° C.) in a glass flask for 2 h using 0.5 and 5 mmol of 2,6-DTBP, substrate to solvent (acetone) molar ratios of 1:270 and 1:27, respectively, a catalyst to substrate ratio of 1:1 and 1:10 (w/w), and adequate amount of 30 wt % aqueous $H_2O_2$ to give substrate to $H_2O_2$ molar ratios of 1:1, 1:2, and 1:6. The products were quantitatively analyzed by means of HP-5890 GC equipped with a FID detector and an 30 m×0.53 mm×0.50 μm fused silica capillary column (SPB-20) using 1, 4-di-tert-butylbenzene as internal standard. The catalytic evaluation results are listed in TABLES III, IV and V respectively.

TABLE III

Oxidation of 2,6-DTBP over Ti-substituted Molecular Sieves[a] as a Function of the Nominal Ti-Loading.

| Catalyst | Ti loading[b] | Conversion, % | Mononuclear Quinone yield, % | Mononuclear Quinone selectivity, % |
|---|---|---|---|---|
| Ti-HMS | 1 | 26 | 14 | 54 |
| (S° I°) | 2 | 55 | 32 | 58 |
| | 5 | 50 | 24 | 48 |
| | 7 | 65 | 31 | 48 |
| | 10 | 98 | 46 | 47 |
| Ti-HMS | 1[c] | 83 | — | 95[d] |
| (S°/S⁺) | | | | |
| Ti-MCM-41 | 1 | 8 | 3 | 38 |
| (S⁺X⁻I⁺) | 1[c] | 20 | — | 98[d] |
| | 2 | 16 | 6 | 37 |
| | 10 | 39 | 18 | 46 |
| Ti-MCM-41 | 1 | 21 | 7 | 34 |
| (S⁺I⁻, by | 2 | 22 | 9 | 39 |
| prior art) | 5 | 36 | 15 | 42 |
| TS-1 | 1 | 3 | — | — |
| (S⁺I⁻, by prior art) | 8 | 24 | 9 | 36 |
| Blank | — | 0.3 | — | — |

[a]unless otherwise specified the reactions were carried out at reflux temperature (62° C.) in a glass flask for 2 h using 5 mmol of 2,6-DTBP, substrate to solvent (acetone) molar ratio of 1:27, catalyst to substrate ratio of 1:10 (w/w) and molar ratio of substrate to peroxide 1:6.
[b]nominal Ti loading.
[c]this reaction was carried out using 0.5 mmol of 2,6-DTBP, substrate to solvent (acetone) molar ratio to 1:270, caralyst to substrate ratio of 1:1 (w/w) and molar ratio of substrate to peroxide 1:6.
[d]total quinone (monomer and dimer) selectivity.

Table III provides a comparison of the catalytic activities of Ti-HMS, prepared by (S°I°) and (S°/S⁺) templating, Ti-MCM-41 (prepared by (S⁺X⁻I⁺) templating) and prior art Ti-MCM-41 (S⁺I⁻) and TS-1 molecular sieves for the peroxide oxidation of 2,6-DTBP to the corresponding quinone. At a titanium substitution level of 1 mole %, Ti-HMS (S°I°) affords 26% conversion of the substrate with 54 % selectivity to the mononuclear quinone under the reaction conditions provided in the TABLE footnote. Ti-MCM-41 (S⁺X⁻I⁺) and prior art Ti-MCM-41 (S⁺I⁻) and TS-1 under equivalent conditions are substantially less reactive, affording substrate conversions of only 8, and 3 %, respectively. The extremely low conversion in the case of TS-1 is explained by the small pore size (≈6 Å) of the silicalite host which prevents the substrate from accessing the intracrystal titanium centers. However, access to Ti-MCM-41 relative to Ti-HMS seems to be related mainly to the absence of complementary textural mesoporosity (see Examples 2,15–18) and to some differences in titanium siting. It may be that the much larger wall thickness of Ti-HMS as relative to Ti-MCM-41 results in titanium bond angles that enhance the reactivity of the peroxotitanyl intermediate.

The data in Table III also show that the activity of Ti-HMS increases as the titanium loading is increased to 10 mole %. Above 10% titanium substitution, the conversion begins to decrease. We should note that these titanium loadings are nominal values and do not necessarily correspond to the framework content of titanium. Nevertheless, the thicker-walled, small scattering domain size (complementary textural mesoporosity) Ti-HMS derivatives prepared by S°I° templating are much more reactive than their thin-walled, electrostatically templated Ti-MCM-41 counterparts at all titanium loading levels over the range of 1–10 mole %.

TABLE IV

Catalytic Activity of 10% Ti-HMS (S°I°) as a Function of the Substrate:$H_2O_2$ Molar Ratio[a]

| Substrate:$H_2O_2$ (mol/mol) | Conversion, % | Mononuclear Quinone yield, % | Mononuclear Quinone selectivity, % |
|---|---|---|---|
| 1:1 | 14 | 5 | 36 |
| 1:2 | 30 | 10 | 33 |
| 1:6 | 98 | 46 | 47 |

[a]Reaction conditions are the same as in TABLE III (footnote a).

The results in Table IV illustrate that the conversion of 2,6-DTBP over 10% Ti-HMS increases as the substrate:$H_2O_2$ mole ratio is increased from 1:1 to 1:6. Interestingly, the selectivity toward the mononuclear quinone remains in the 33–47% range even though the conversion ranges from 14–93%. Other products formed in the reaction include the dealkylated quinone and the binuclear di-tert-butyl quinone, but there are not included in the quinone selectivities reported in the Table.

TABLE V

Catalytic Activity of 1% Ti-HMS (S°I°) as a Function of the Template Removal Method.[a]

| Method of Template Removal | Conversion, % | Quinone yield, % |
|---|---|---|
| Calcined | 26 | 14 |
| Ethanol extracted | 7 | 5 |
| As-synthesized | 4 | 3 |

[a]Reaction conditions are the same as in TABLE III (footnote a).

Since the neutral amine template (S°) used in the synthesis of Ti-HMS can be removed by simple solvent extraction, we have an unique opportunity to compare the effects of calcination on the intrinsic reactivities of the site isolated titanium centers. As shown by the first two entries in TABLE V, 1% Ti-HMS that has been calcined at 650° C. for 4 h to remove the template is substantially more reactive than the same derivative subjected to template removal by solvent extraction. Thus, calcination plays an important role in the siting and the reactivity of the framework titanium centers. We also note from the data in TABLE III that the as-synthesized (air-dried) Ti-HMS, which is still loaded with neutral amine template, also is active for peroxide oxidation. Apparently, the substrate is capable of competing with the neutral surfactant for adsorption sites adjacent to the titanium centers.

EXAMPLE 17

This example illustrates the effect of the calcination temperature of the 1% Ti-loaded mesoporous molecular sieves on the catalytic activity in the peroxide oxidation of 2,6-DTBP.

TABLE VI

Effect of the Calcination Temperature and Templating Method on the Activity and Selectivity for 2,6-DTBP oxidation[a] of a different 1% Ti-substituted mesoporous metallosilicates.

| Catalyst | Calcination temperature, ° C. | Conversion, % | Mononuclear Quinone Yield, % | Mononuclear Quinone selectivity, % |
|---|---|---|---|---|
| Ti-HMS (S°I°) | 450 | 48 | 28 | 50 |
|  | 540 | 57 | 32 | 60 |
|  | 650 | 80 | 50 | 62 |
| Ti-MCM-41 ($S^+X^-I^+$) | 540 | 34 | 12 | 36 |
|  | 650 | 42 | 18 | 44 |

[a]reaction conditions are the same as in TABLE III (footnote c).

Two trends are evident from the data in the TABLE: the higher calcination temperature affords (i) larger conversions of substrate over both materials; (ii) larger quinone-monomer yields and (iii) larger selectivities to quinone-monomer. It is also noteworthy that Ti-HMS, prepared by neural templating exhibits much larger catalytic activities than the electrostatic Ti-MCM-41 counterpart at any calcination temperature.

EXAMPLE 18

This example describes the neutral (S°I°) preparation and the catalytic activity of a V-substituted silicate mesoporous molecular sieve (denoted V-HMS).

In a typical preparation 6.83 g of TEOS were added to 15 ml of EtOH. A solution of 1.24 g of DDA in 10 ml of EtOH was added to a solution of 0.060 g of $Na_3VO_4$ in 100 ml of deionized $H_2O$ under vigorous stirring. The ethanol solution of TEOS was added to the above template solution gradually under vigorous stirring. The molar composition of the reaction mixture per mole of $SiO_2$ was:

0.005 moles $V_2O_5$
0.20 moles $C_nH_{2n+1}NH_2$
42.6 moles $H_2O$
6.5 moles EtOH.

Figure 10:
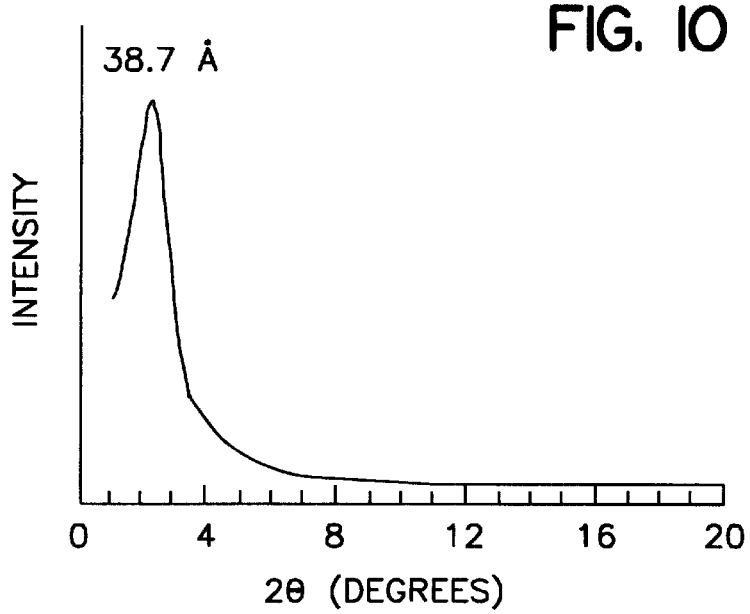
FIG. 10 is an X-ray powder diffraction pattern of the calcined product of Example 18.

The resultant reaction mixture was stirred at ambient temperature for 24 hours to obtain the crystalline V-HMS product. The product was filtered, air dried and calcined at 650° C. for 4 h. The X-ray diffraction pattern of the calcined product of this example is shown in FIG. 10. It exhibits a single strong reflection centered at 39±1.0 Å. The scattering domain size of this sample is nearly identical to that exhibited by Ti-HMS. The BET surface area obtained from nitrogen adsorption measurements is 1209 $m^2$/g. The Horvath Kawazoe pore size distribution is centered at 24 Å and the corresponding framework wall thickness is 21 Å.

The calcined product of this example was used in peroxide oxidation and hydroxylation of both 2,6-DTBP and benzene. The reactions involving 2,6-DTBP were carried out at the same conditions as described in TABLE III (footnote a). The total conversion of 2,6-DTBP is 49 mol %. Surprisingly, the major product from 2,6-DTBP oxidation is the 3,3', -5,5'-TTB-4,4'-DPQ dimer. The yield of the 3,3,'5, 5'-TTB-4,4'-DPQ is determined to be 40 mol %, while that of the mononuclear quinone-2,6-DTBBQ is virtually zero mol %. The significance of this example is that V-HMS is extremely selective toward the dimeric 3,3',5,5'-TTB-4,4'-DPQ, whereas Ti-HMS, in contrast, is much more selective toward the monomeric quinone-2,6-DTBBQ.

The hydroxylation of benzene was carried out at 72° C. for 24 h using 100 mmol of benzene as substrate, catalyst to substrate ratio of 1:372 (w/w) and substrate to hydrogen peroxide molar ratio of 3:1. This reaction was carried out in the absence of solvent. The only product from benzene hydroxylation over V-HMS is phenol. The turnover number for this reaction is 77 mol/mol V over 24 h.

EXAMPLE 19

Figure 11:
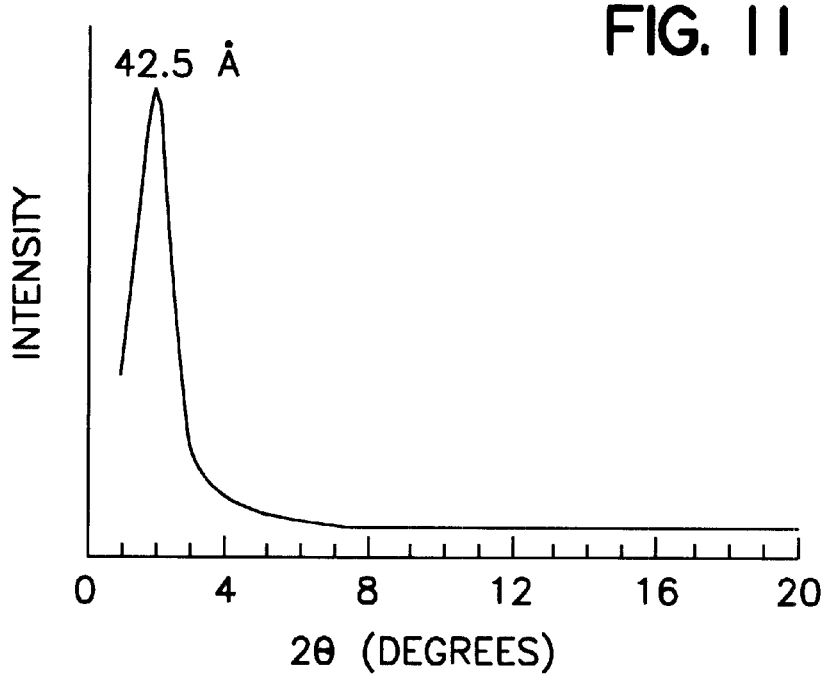
FIG. 11 is an X-ray powder diffraction pattern of the calcined product of Example 19.

This example describes the neutral (S°I°) preparation of Cr-substituted mesoporous molecular sieve (denoted Cr-HMS) and its catalytic activity for 2,6-Di-tert-butyl phenol oxidation and benzene hydroxylation in the presence of 30 wt % aqueous $H_2O_2$ as oxidant. The preparation procedure is essentially the same as described in Example 18, with $CrO_3$ (instead of $Na_2VO_4$) used as transition metal precursor. The molar composition of the reaction mixture per mole of $SiO_2$ was:

0.01 moles $CrO_3$
0.20 moles $C_nH_{2n+1}NH_2$
42.6 moles of $H_2O$
6.5 moles of EtOH The XRD pattern of the calcined product is shown in FIG. 11. It exhibits a strong $d_{100}$ reflection at 42±1.0 Å d-spacing. The scattering domain size of this sample is nearly identical to that reported for Example 3. The BET surface area is 1080 $m^2/g$. The size of the framework-confined mesopores, as determined from the Horvath-Kawazoe pore size distribution curve, is 26 Å and the corresponding framework wall thickness is again much larger (22 Å) than that exhibited by the prior art Pathway 1 MCM-41 samples (usually, around 8–12 Å).

The calcined Cr-HMS catalyst of this example was used for both 2,6-DTBP oxidation and benzene hydroxylation. Both reactions were carried out at the same conditions as described in Example 18. The major product from the 2,6-DTBP oxidation is the 3,3',5,5'-TTB-4,4'-DPQ dimer. However, the selectivity toward the dimer, for this particular example, is much lower than that exhibited by V-HMS (see Example 18). On the other hand the selectivity toward the monomer relative to the Ti-HMS analog is lower. The total 2,6-DTBP conversion is 85 mol % with 2,6-DTBBQ monomer yield of 22 mol % and 3,3',5,5'-TTB-4,4'-DPQ dimer yield of around 53 mol %.

As in the case of V-HMS, the only product obtained from benzene hydroxylation is phenol. The turnover number for Cr-HMS is also similar to that observed for V-HMS (75 mol/mol Cr over 24 h).

EXAMPLE 20

Figure 12:
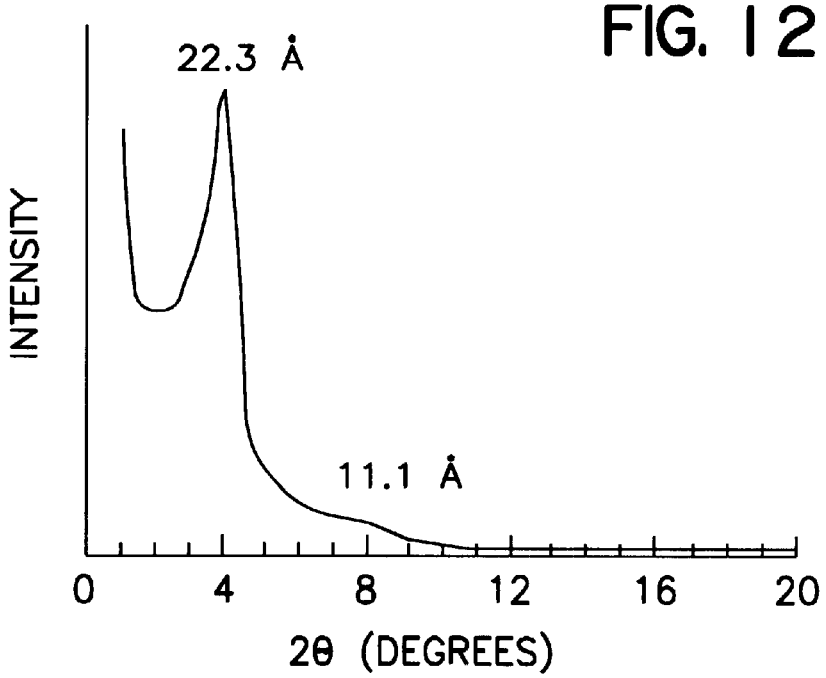
FIG. 12 is an X-ray powder diffraction pattern of the calcined product of Example 20.

This example describes the neutral (S°—S°I°) direct synthesis of pillared lamellar Ti-substituted silicate molecular sieve (denoted Ti-PLMS) with mixed intergallery-confined micropores and textural mesopores and its catalytic activity for 2,6-DTBP oxidation and benzene hydroxylation with 30 wt % aqueous $H_2O_2$ as oxidant. All the preparation procedures are the same as Example 3 except the surfactant solution. Instead of a neutral primary amine (S°) template (dodecylamine), a solution of 3.535 g of a neutral dipolar diamine (S°—S°) template, in particular 1,12-diaminododecane, in 100 ml of water and 10 ml of ethanol was used to prepare the Ti-substituted crystalline silicate with a pillared layered structure. Such templates would most likely organize in a layered fashion and should provide for the preparation of a new class of stable layered metallosilicate molecular sieve structures. The molar composition of the reaction mixture per mole of $SiO_2$ was:

0.01 moles $TiO_2$
0.26 moles $NH_2C_nH_{2n+1}NH_2$
42.68 moles $H_2O$
9.80 moles EtOH
1.95 moles i-PrOH The product was filtered, air dried and calcined. It is noteworthy that the neutral diamine template (S°—S°) can also be solvent extracted in a manner similar to that described in Example 9. In contrast to the recently reported templated layered phases (Stucky et al., Nature, 368, 317–321 (1994)) our diamine templated lamellar metallosilicate was stable after calcination at 650° C. for 4 h. The XRD pattern of the calcined product of this example is shown in FIG. 12. It exhibits a relatively strong $d_{100}$ reflection at 22±1.0 Å d-spacing and a second order (002) reflection at 11±2.0 Å. In addition, this sample exhibits unusually high specific surface area of 978 $m^2/g$ (typical for mesoporous molecular sieves) and adsorption properties (see FIG. 13) typical for a pillared layered materials (a well expressed hysteresis loop of type H4). The t-plot revealed that almost half of this specific surface area is due to the presence of intergallery-confined micropores.

The calcined Ti-PLMS product was used as catalyst for 2,6-DTBP oxidation. The reaction conditions were the same as described in TABLE III (footnote a). The total conversion of 2,6-DTBP is only about 25% mol with yield of 2,6-DTBBQ of about 10 mol % and that of the 3,3',5,5'-TTB-4,4'-DPQ dimer of also approximately 10 mol %. It is obvious that the lamellar Ti-silicate is much less reactive than the hexagonal metallosilicate analogs. This could be attributed to totally different pore structure for this lamellar metallosilicate and to a different titanium siting as compared to the hexagonal mesoporous analogs.

The calcined product of this example was also used as a catalyst for benzene hydroxylation. The reaction was carried out as described in Example 18. The only GC detectable product here is phenol. The turnover number of benzene to phenol is 6.4 mol/mol Ti over a 24 h period. It should be emphasized that this particular reaction was performed in the absence of any polar solvent.

We claim:

1. A mesoporous metal silicate molecular sieve composition, wherein the metal is present in place of some of the silicon in the silicate and capable of undergoing a change of oxidation number in an oxidation or reduction reaction with an organic molecule having a kinetic diameter greater than 6 Å, a scattering domain size of less than about 400 Å, a ratio of textural to framework-confined mesoporosity of at least about 0.2 and a specific surface area of 300 to 1500 square meters per gram, which composition is prepared from a template consisting essentially of a neutral molecule and an inorganic oxide precursor and then the template is removed and has an x-ray diffraction pattern selected from the group consisting of FIGS. 2, 4, 10, 11 and 12.

Figure 13:
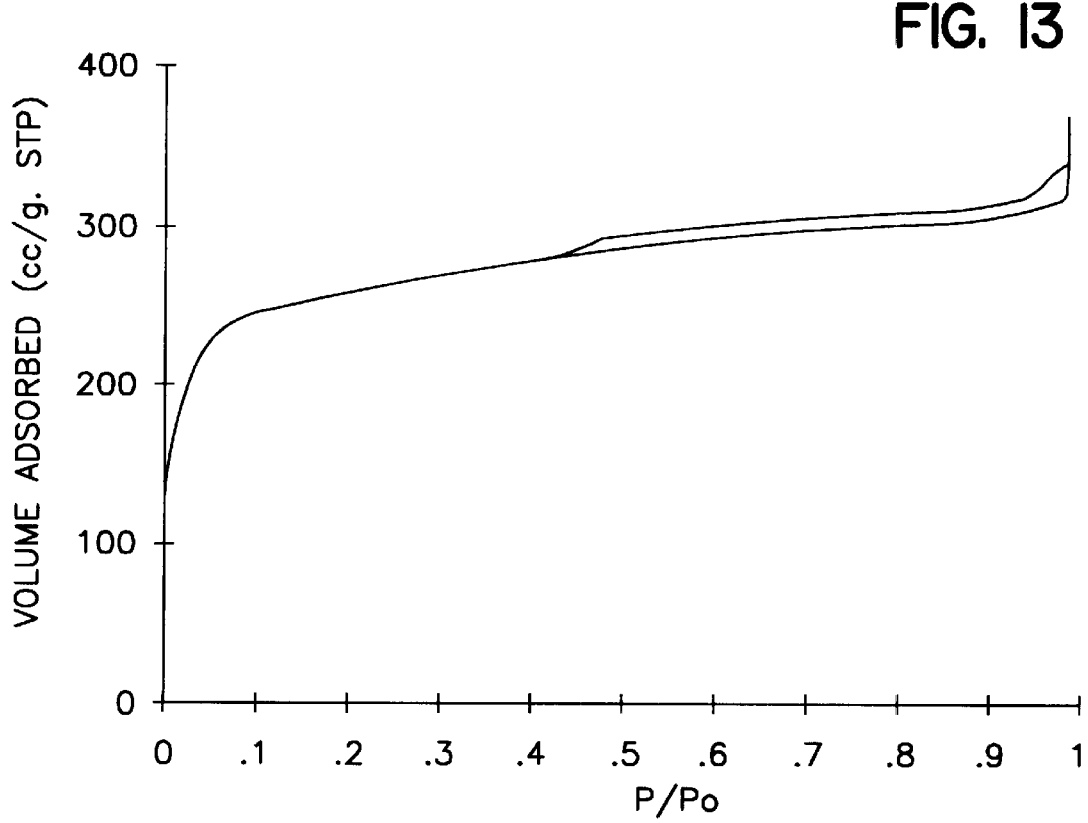
FIG. 13 is a $N_2$ adsorption-desorption isotherm of the calcined product of Example 20.

2. The composition of claim 1 having $N_2$ adsorption-desorption isotherms and Horvath-Kawazoe pore size distribution as shown in FIG. 13.

3. The composition of claim 1 wherein the molar ratio of neutral template to total inorganic oxide precursors in the as-synthesized crystalline metal silicate is between about 0.05 and 3.

4. The composition of claim 3 wherein the metal silicate molecular sieve in its anhydrous state has the formula:

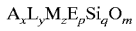

wherein A is optional and is at least one divalent element selected from the group consisting of Mg, Zn and Cu; L is optional and is at least one element selected from the group consisting of B, Al, Ga, Cr and Fe; M is optional and is at least one element other than silicon selected from the group consisting of Ti, V, Sn, Zr and Ge; E is optional and is at least one element selected from the group consisting of V, Cr, W and Mo; O is oxygen and x, y, z, p, q and m are the molar parts of A, L, M, E, Si and O, respectively, wherein there is at least one of A, L, M or E and wherein, x is between 0 and 0.25; y is between 0 and 0.5; z is between 0 and 0.5; p is between 0 and 0.5, q is between 0.5 and 1 and m is about 2.

5. A composite material prepared from the calcined composition of claim 1 admixed with material selected from the group of the amorphous, and crystalline solids.

6. A mesoporous metal silicate molecular sieve composition, wherein the metal is present in place of some of the silicon in the silicate and capable of undergoing a change of oxidation number in an oxidation or reduction reaction with an organic molecule having a kinetic diameter greater than 6 Å, prepared by a neutral self-assembly method which comprises reacting a template consisting of a neutral molecule and neutral inorganic oxide precursors in the presence of hydrolyzing agent as a solvent and optionally a co-solvent with the hydrolyzing agent to form a reaction product, aging of the reaction mixture at reaction conditions which form the crystalline metallosilicate and removal of the template and the aqueous solution, wherein the composition has an x-ray diffraction pattern selected from the group consisting of FIGS. 2, 4, 10, 11 and 12.

7. The composition of claim 6 in which the self-assembly method is modified so that it comprises reacting of the inorganic oxide precursors with partially protonated template in the presence of acid, hydrolyzing agent and the optional co-solvent to form a reaction product, aging of the reaction mixture at reaction conditions which form the mesoporous crystalline metal silicate and removal of the template and the aqueous solution.

8. The composition of claim 6 in which the neutral template has been removed and recycled by solvent extraction.

9. A mesoporous metal silicate molecular sieve composition, wherein the metal is present in place of some of the silicon in the silicate and capable of undergoing a change of oxidation number in an oxidation or reduction reaction with an organic molecule having a kinetic diameter greater than 6 Å, a scattering domain size of less than about 400 Å, a ratio of textural to framework-confined mesoporosity of at least about 0.2 and a specific surface area of 300 to 1500 square meters per gram, prepared by a mediated templating method which comprises reacting of an acidic solution of quaternary ammonium cationic template and inorganic oxide precursors in the presence of hydrolyzing agent as a solvent and optionally a co-solvent with the hydrolyzing agent to form a reaction product, aging of the reaction mixture at mild reaction conditions to form the hexagonal mesoporous metal silicate product and removal of the template and the aqueous solution, wherein the composition has an x-ray diffraction pattern selected from the group consisting of FIGS. 2, 4, 10, 11 and 12.

10. The composition of claim 9 which has an X-ray diffraction pattern with a d-spacing of at least about 15 Å.

11. The composition of claim 9 wherein the molar ratio of quaternary ammonium template to total metallosilicate oxide precursors in the as-synthesized crystalline form is between about 0.05 and 3.

12. The composition of claim 11 wherein the hexagonal metal silicate molecular sieve in its as-synthesized and anhydrous state has the formula:

$$A_xL_xM_xE_pSi_qO_m$$

wherein A is optional and is at least one divalent element selected from the group consisting of Mg, Zn and Cu; L is optional and is at least one element selected from the group consisting of B, Al, Ga, Cr and Fe; M is optional and is at least one element other than silicon selected from the group consisting of Ti, V, Sn, Zr and Ge; E is optional and is at least one element selected from the group consisting of V, Cr, W and Mo; O is oxygen and n, x, y, z, p, q and m are the molar parts of $S^+$, K, L, M, N, Si and O, respectively, and wherein, x is between 0.001 and 0.2; y is between 0.001 and 0.5; z is between 0.001 and 0.5; p is between 0.001 and 0.5, q is between 0.5 and 1 and m is about 2.

13. The composition of claim 12 wherein M is Ti or V or Sn and z is between about 0.001 and 0.25.

14. The composition of any one of claims 6 or 7 wherein said hexagonal or hexagonal-like mesoporous metal silicate has a framework wall thickness of at least about 17 Å and a very small scattering domain size of less than about 400 Å.

15. The composition of claim 14 wherein said hexagonal or hexagonal-like mesoporous metal silicate has, after template removal by solvent extraction or calcination or a combination thereof, a $N_2$ adsorption-desorption isotherm with more than one hysteresis loop and textural to framework-confined mesoporosity ratio larger than about 0.2.

16. The composition of claim 4 wherein L is Al and y is between about 0.001 and 0.2.

17. The composition of claim 4 wherein L is Cr and y is between about 0.001 and 0.25.

18. The composition of claim 4 wherein M is Ti or V or Sn and z is between about 0.001 and 0.25.

* * * * *

UNITED STATES PATENT AND TRADEMARK OFFICE
CERTIFICATE OF CORRECTION

PATENT NO. : 6,391,278 B1
DATED : May 21, 2002
INVENTOR(S) : Thomas J. Pinnavaia et al.

It is certified that error appears in the above-identified patent and that said Letters Patent is hereby corrected as shown below:

<u>Title page,</u>
Item [57], ABSTRACT,
Line 9, "($\leqq$400Å)" should be -- ($\leq$400Å) --.

Item [56], References Cited, OTHER PUBLICATIONS, "Thangaraj et al." reference "Zeolites, vol. 9, 943" should be -- Zeolites, 12, 943 --.

<u>Column 1,</u>
Line 11, "6, 493, 143 which" should be -- 6, 193, 143 which --.
Line 39, "($\leqq$400Å)" should be -- ($\leq$400Å) --.

<u>Column 3,</u>
Line 26, "U.S. Pat. No. 1747434" should be -- (S.U. Pat. No. 1747434 --.

<u>Column 4,</u>
Line 3, "as ϒ or $Al_2O_3$" should be -- as ϒ or η- $Al_2O_3$ --.
Line 29, "$Na^{30}$, $K^{30}$ or $Ca^{2}$" should be -- Na+, K+ or $Ca^{2+}$ --.

<u>Column 5,</u>
Line 29, "S+1-TS-1" should be -- S-1-TS-1 --.
Line 31, "$Si^{4-}$ for $Al3^{3+}$" should be -- $Si^{4+}$ for $Al^{3+}$ --.

<u>Column 6,</u>
Line 27, "$S^{30}1^-$ electrostatic" should be -- $S^+1^-$ electrostatic --.
Line 29, "zeolite b" should be -- zeolite B --.
Line 34, "exeption of" should be -- exception of --.

<u>Column 7,</u>
Line 52, "via $S^{31}1+$" should be -- via $S^-1^+$ --.
Line 56, "($X^{31}M^+$)" should be -- ($X^-M^+$) --.

<u>Column 8,</u>
Line 39, "($\leqq$400Å)" should be -- ($\leq$400Å) --.

UNITED STATES PATENT AND TRADEMARK OFFICE
CERTIFICATE OF CORRECTION

PATENT NO. : 6,391,278 B1
DATED : May 21, 2002
INVENTOR(S) : Thomas J. Pinnavaia et al.

It is certified that error appears in the above-identified patent and that said Letters Patent is hereby corrected as shown below:

Column 9,
Line 40, "X$^-$1$^+$ route)" should be -- X$^-$1$^+$- templating route) --.

Column 10,
Line 46, "volume ≦0.6 cm$^3$/g" should be -- volume ≤0.6 cm$^3$/g --.

Column 11,
Line 35, "assess" should be -- access --.

Column 12,
Line 47, particle "≦400" should be -- particle ≤400 --.

Column 13,
Line 10, "smaller that the" should be -- smaller than the --.
Line 29, "(≧17Å), small particle size (≦400Å)" should be -- (≥17Å), small particle size (≤400Å) --.

Column 14,
Line 3, "size (≦400Å)" should be -- size (≤400Å) --.
Line 46, "9 is a N adsorption" should be -- 9 is a N$_2$ adsorption --.
Line 63, "(≧17Å), small elementary particle size "(≦400Å)" should be -- (≥17Å), small elementary particle size (≤400Å) --.

Column 15,
Line 29, "thickness of ≧17Å" should be -- thickness of ≥17Å) --.
Line 31, size "≦400Å" should be -- size ≤400Å --.
Line 32, "typically ≧0.2" should be -- typically ≥0.2 --.

Column 16,
Line 20, "t-bonding" should be -- H-bonding --.
Line 36, "thickness (≧17Å)" should be -- thickness of (≥17Å) --.
Line 37, "size ≦400Å" should be -- size ≤400Å --.

UNITED STATES PATENT AND TRADEMARK OFFICE
CERTIFICATE OF CORRECTION

PATENT NO. : 6,391,278 B1
DATED : May 21, 2002
INVENTOR(S) : Thomas J. Pinnavaia et al.

It is certified that error appears in the above-identified patent and that said Letters Patent is hereby corrected as shown below:

Column 18,
Line 44, "buthanol" should be -- butanol --.

Column 19,
Line 19, "template (S°)" should be -- template (S$^+$) --.
Line 30, "smaller that the" should be -- smaller than the --.

Column 20,
Line 44, "diamines (S° 13 S°)" should be -- diamines (S°-S°) --.

Column 21,
Line 34, "sil wa based" should be -- silica based --.
Line 51, "-tetrakyl orthotitanate" should be -- tetraethyl orthotitanate --.
Line 66, "3,3,5,5,-TTB-4,4'-DPQ-3,3,5,5" should be -- 3,3',5,5'-TTB-4,4'-DPQ-3,3',5,5' --.

Column 22,
Line 34, "S$^+$I$^{31}$ (Pathway 1)" should be -- S$^+$I$^-$ (Pathway) --.

Column 27,
Line 25, "T-O-Si" should be -- Ti-O-Si --.

Column 29,
Line 24, "14-93%" should be -- 14-98% --.

Column 32,
Line 12, "strong $d_{100}$" should be -- strong $d_{001}$ --.

Signed and Sealed this

Twenty-fourth Day of June, 2003

JAMES E. ROGAN
*Director of the United States Patent and Trademark Office*